(12) United States Patent
Stubbs et al.

(10) Patent No.: US 9,014,787 B2
(45) Date of Patent: Apr. 21, 2015

(54) BIOABSORBABLE TARGET FOR DIAGNOSTIC OR THERAPEUTIC PROCEDURE

(75) Inventors: James B. Stubbs, Alpharetta, GA (US); George D. Hermann, Portola Valley, CA (US); Gail S. Lebovic, Frisco, TX (US); Michael J. Drews, Palo Alto, CA (US)

(73) Assignee: Focal Therapeutics, Inc., Boston, MA (US)

( * ) Notice: Subject to any disclaimer, the term of this patent is extended or adjusted under 35 U.S.C. 154(b) by 434 days.

(21) Appl. No.: 12/790,314

(22) Filed: May 28, 2010

(65) Prior Publication Data

US 2011/0004094 A1    Jan. 6, 2011

Related U.S. Application Data

(60) Provisional application No. 61/183,010, filed on Jun. 1, 2009.

(51) Int. Cl.
*A61B 5/05*    (2006.01)
*A61B 19/00*   (2006.01)
*A61N 5/10*    (2006.01)
*A61B 17/00*   (2006.01)

(52) U.S. Cl.
CPC .............. *A61B 19/54* (2013.01); *A61N 5/1049* (2013.01); *A61B 2017/00004* (2013.01); *A61B 2017/00716* (2013.01); *A61B 2019/446* (2013.01); *A61B 2019/4878* (2013.01); *A61B 2019/5408* (2013.01); *A61B 2019/5425* (2013.01); *A61B 2019/5454* (2013.01)

(58) Field of Classification Search
None
See application file for complete search history.

(56) References Cited

U.S. PATENT DOCUMENTS

| | | |
|---|---|---|
| 3,157,524 A | 11/1964 | Artandi |
| 3,520,402 A | 7/1970 | Nichols et al. |
| 5,019,087 A | 5/1991 | Nichols |
| 6,030,333 A | 2/2000 | Sioshansi et al. |
| 6,159,165 A | 12/2000 | Ferrera et al. |
| 6,161,034 A | 12/2000 | Burbank et al. |
| 6,174,330 B1 | 1/2001 | Stinson |
| 6,214,045 B1 | 4/2001 | Corbitt, Jr. et al. |
| 6,356,782 B1 | 3/2002 | Sirimanne et al. |
| 6,371,904 B1 | 4/2002 | Sirimanne et al. |
| 6,638,308 B2 | 10/2003 | Corbitt, Jr. et al. |
| 6,766,186 B1 | 7/2004 | Hoyns et al. |
| 6,881,226 B2 | 4/2005 | Corbitt, Jr. et al. |
| 7,047,063 B2 | 5/2006 | Burbank et al. |

(Continued)

OTHER PUBLICATIONS

International Search Report, from corresponding PCT/US10/036828, mailed Jul. 28, 2010.

(Continued)

*Primary Examiner* — Long V Le
*Assistant Examiner* — Bradley Impink
(74) *Attorney, Agent, or Firm* — Morrison & Foerster LLP

(57) ABSTRACT

An implantable device has a body that is substantially rigid and has an imageable shape. The body is further bioabsorbable and may contain permanent metallic elements to aid in its imaging. When the device is implanted in a resected cavity in soft tissue, it can cause the cavity to conform substantially to a known imageable shape. The implantable device is further imageable due to its attenuation properties being different from those of soft tissue such that the boundaries of the tissue corresponding to the predetermined shape can be determined.

16 Claims, 32 Drawing Sheets

(56) References Cited

U.S. PATENT DOCUMENTS

| | | |
|---|---|---|
| 7,229,417 B2 | 6/2007 | Foerster et al. |
| 7,637,948 B2 | 12/2009 | Corbitt, Jr. |
| 7,837,612 B2 | 11/2010 | Gill et al. |
| 7,875,059 B2 | 1/2011 | Patterson et al. |
| 2001/0041936 A1 | 11/2001 | Corbitt, Jr. et al. |
| 2004/0049269 A1 | 3/2004 | Corbitt, Jr. et al. |
| 2005/0049489 A1 | 3/2005 | Foerster et al. |
| 2005/0074405 A1 | 4/2005 | Williams, III |
| 2005/0101860 A1 | 5/2005 | Patrick et al. |
| 2005/0165480 A1 | 7/2005 | Jordan et al. |
| 2006/0058570 A1 | 3/2006 | Rapach et al. |
| 2006/0173296 A1 | 8/2006 | Miller et al. |
| 2007/0021642 A1 | 1/2007 | Lamoureux et al. |
| 2007/0038014 A1* | 2/2007 | Cox et al. .................. 600/8 |
| 2007/0167668 A1 | 7/2007 | White et al. |
| 2008/0243226 A1 | 10/2008 | Fernandez et al. |
| 2009/0024225 A1 | 1/2009 | Stubbs et al. |
| 2009/0030298 A1 | 1/2009 | Matthews et al. |
| 2010/0042104 A1 | 2/2010 | Kota et al. |
| 2013/0289390 A1* | 10/2013 | Hermann et al. ............ 600/424 |

OTHER PUBLICATIONS

Lakeshore Biomaterials, Mechanical Properties chart.
Lakeshore Biomaterials, Tailoring of Poly(lactide-co-glycolide) to Control Properties.
Medical Device Daily, 9(188):1, 9 (Sep. 30, 2005).
Purac Biomaterials, Purasorb Technology.
International Preliminary Report on Patentability mailed Dec. 15, 2011 for Application No. PCT/US2010/036828 (8 Pages).
International Search Report and Written Opinion for PCT Application No. PCT/US13/38145, mailed Jul. 9, 2013 (21 pages).

* cited by examiner

SECTION B-B

SECTION C-C

SECTION A-A

SECTION B-B

SECTION E-E

SECTION B-B

SECTION D-D

SECTION A-A

BIOABSORBABLE TARGET FOR DIAGNOSTIC OR THERAPEUTIC PROCEDURE

RELATED APPLICATIONS

This application claims priority to U.S. Provisional Patent Application No. 61/183,010, filed on Jun. 1, 2009, and entitled Bioabsorbable Target for Diagnostic or Therapeutic Procedure, which application is incorporated by reference in its entirety.

This application incorporates by reference United States patent publication no. 2009-0024225-A1, entitled "Implant for Targeting Therapeutic Procedure," filed on Jul. 16, 2008, which application is incorporated herein by reference in its entirety.

BACKGROUND

Two trends have become significant in driving the delivery of medical treatments: 1) treatments, be they drugs, energy or surgery, are moving towards local and focal delivery, and 2) treatments are being tailored and optimized for each patient based on their specific anatomy, physiology and disease features. These directions both are designed to minimize the likelihood of adverse effects from the therapies as well as provide a more patient-specific treatment, which may improve disease-free survival rates and/or improve disease recurrence.

These trends began in surgery where large, open surgical procedures have been and continue to be replaced by minimally-invasive procedures and endoscopic procedures. Drug therapies are moving toward more localized delivery as well, such as treatments that are placed directly at or near the treatment site (e.g., drug eluting stents and Gliadel wafers for brain tumors). Until recently, the desire to do the same in radiation therapy has been hampered by inadequate technology for focused delivery. However, significant progress in local radiation delivery has been accomplished in the brachytherapy subspecialty of radiation oncology, most notably in prostate and breast cancer patients. In breast brachytherapy, the radiation source is temporarily inserted into a temporarily placed catheter inside the breast and the appropriated dose of radiation is delivered from the "inside out". This approach has gained popularity because it offers a number of benefits to patients undergoing treatment for breast cancer including delivery in a shorter timeframe and delivery to a smaller volume of the breast tissue (i.e., accelerated and smaller volume treatments).

External beam radiation therapy (EBRT) is one of the most common adjuvant therapies for cancer patients in the U.S., with chemotherapy being the other one. EBRT is delivered to cancer patients as either the first line of therapy (for non-resected cancers) or as a means of maximizing local control of the cancer following surgical removal of the tumor. In EBRT, one or more beams of high energy x-rays are aimed at the part of the body needing radiotherapy. A linear accelerator (often called a linac) produces the beams and has a collimator that helps to shape the beams as they exit the linac. It is very common for a tumor to be treated using two or more beams, each of which is delivered from different directions around the tumor, and that all intersect at the tumor site. In this manner, the tissue surrounding the target can be exposed to lower radiation doses than the sum of the treatment beams yields at the tumor target. The tumor target volume is delineated by the radiation oncologist using CT scans (or other imaging methods such as ultrasound or MRI) of the patient. The tumor target volume and radiation dose prescription parameters are entered into a treatment planning computer. Treatment planning software (TPS) then produces a plan showing how many beams are needed to achieve the radiation oncologist's prescription dose, as well as the size and shape of each beam.

The complete course of EBRT is divided (called fractionation) into numerous small, discrete treatments called fractions. A typical prescribed dose of 60 Gray (Gy) is fractionated into 30 daily treatments of 2 Gy per day. During a fraction, the treatment beam may be "on" for ~1 minute. Thus, the full radiotherapy treatment takes about 6 weeks (5 fractions per week) to complete.

Historically, EBRT has been practiced exactly as has chemotherapy, namely, the radiation doses delivered to the patient are limited only by the tolerance of normal tissues surrounding the site to be treated. Hence, often, the radiation therapy is continued until side-effects become intolerable for the patient. Effectively, radiation therapy has been a "radiate until the patient can't take it anymore" type of treatment. The target volume, in which it is desired to deliver essentially 100% of the prescribed radiation dose, has historically been defined as the tumor (the gross tumor volume, or GTV) plus a surrounding volume of tissue margin that may harbor remaining microscopic tumor cell foci (the clinical target volume, or CTV). Another margin of surrounding normal tissue is added to the CTV to account for errors in positioning of the patient for therapy and movement of the tumor site both during a fraction and between fractions. Chest and upper abdomen radiation therapy (e.g., lung cancer and pancreatic cancer) are two examples where large margins are needed to make sure that the changes in tissue position during respiration do not result in the target leaving the beam during some portion of the fraction delivery.

In the last few years, the treatment planning software and linear accelerator technology have dramatically improved in their ability to shape the radiation therapy beams to better avoid nearby sensitive structures. The latest treatment planning software allows the radiation oncologist and medical physicist to define the volume of tissue to be treated using CT scans and provide therapy constraints (e.g., minimum radiation dose inside the target volume, maximum radiation dose to structures nearby target volume). The software then automatically computes the beam angles and shapes in a process called inverse treatment planning. This process can be even further refined using a technique called Intensity Modulated Radiation Therapy (IMRT) which shapes the beam of radiation. Another feature of the newer linacs is a type of radiographic (and/or ultrasonic) imaging that is used to better position the patient and his/her tumor for more accurate targeting of the treatment beams. This latter method is called Image Guided Radiation Therapy, or IGRT.

Both IMRT and IGRT techniques use numerous, smaller and more precisely shaped beams that intersect at the target volume. IGRT differs from IMRT in at least one important aspect—imaging prior to each fraction is used to reduce positioning errors and make sure the treatment beam is properly targeted. Typically, IGRT uses bony anatomy (e.g., pelvic bones for prostate patients) for radiographic targeting and soft tissue interfaces (e.g., prostatic capsule and bladder wall) for ultrasound targeting. Rarely, implanted radio-opaque markers (e.g., Visi-Coil) have been used to facilitate targeting for IGRT. However, using a definitive target in order to define the limits or margins of treatment area has not been accomplished. In the treatment of breast cancer specifically, some clinicians have attempted to help delineate the margins of the lumpectomy cavity by using radio-opaque markers such as surgical clips placed at the time of surgery. This, in theory, would help the radiation oncologist in treatment planning, however, often these clips are inaccurate in their placement and have a tendency to migrate postoperatively due to healing and scarring. In addition, these markers have not been used for targeting in the newer delivery methods, such as for each fraction or each beam of every fraction as is done in IGRT.

IMRT uses a special type of collimator, a multi-leaf collimator (MLC) that changes the shape of the beam during each fraction to modulate or "sculpt" the radiation dose to more closely fit the actual target volume shape in three dimensions. Linacs with MLCs can control the size and shape of the beam to within a few millimeters accuracy.

IGRT is a relatively new option on linacs. New linacs are being sold today that have on-board imaging capability via mega-voltage (MV) or kilo-voltage (KV) x-rays/fluoroscopy. The on-board imaging capability can also be retrofitted to existing linacs. On-board imaging is a technical capability that has been introduced into the newest linac product lines by all the major linac manufacturers (e.g., Varian Medical Systems, Elekta, Tomotherapy, Accuray and Siemens). While the technology made by these companies provides the possibility of performing better targeting for external beam radiation therapy, the targets (e.g., bony anatomy) are inadequate in order to achieve a precise and accurate target region for treatment.

As described above, targeting the external beam radiation therapy accurately requires one to point out the target using fiducial markers having different radiographic properties than that of surrounding tissue (e.g., bone, and soft tissue). To date, this has been accomplished using radio-opaque markers (e.g., permanently implanted foreign bodies). Alternatively, Patrick and Stubbs described a device and method for shaping and targeting EBRT using a temporarily implanted balloon catheter (U.S. Pat. No. 7,524,274). This device and method required implantation of a foreign body whose removal necessitated a second medical procedure. There is clinical evidence suggesting that the implantation and irradiation of an area of the breast surrounding an implanted balloon can result in long-standing complications such as persistent seroma (collection of fluid within the breast that may become infected).

Hence, the need exists for a better device and method for positioning the target volume and providing a visual target for the external beam treatments, without requiring subsequent removal.

SUMMARY

The present invention includes methods, as well as devices and systems, for the targeting and delivery of therapeutic rays to regions of tissue within a patient, or for improving the accuracy and precision of such methods, devices and systems. In its first aspect, the invention includes a method for treating a proliferative tissue disease in a patient. The method includes excising diseased tissue from the patient and thereby creating a tissue cavity. A bioabsorbable implant formed from an injection molded bioabsorbable thermoplastic is then placed within the tissue cavity. The implant can have a deformable but predetermined shape and includes a means for visualizing and, in some cases, orienting the device within the surgical cavity. The location of the implant within the patient can then be easily determined and the region of tissue surrounding the lumpectomy cavity (margin) can be more accurately treated with therapeutic energy sources.

In other embodiments, the bioabsorbable implant can be hollow. Alternatively, the hollow implant can be filled with a material having a density less than a density of soft tissue. The filler material can alternatively have a density less than 1.03 g/cm³. The bioabsorbable implant can also include an imageable element located in a geometric center of the implant.

Additional embodiments include a bioabsorbable implant in the shape of a sphere.

In certain embodiments, the bioabsorbable implant is formed of two halves coupled together before implantation.

In another embodiment, the bioabsorbable implant includes a plurality of arms emanating from a center of the implant. The arms can have end caps contacting tissue around the cavity to maintain a desired shape of the cavity while still allowing seroma to pass through between the end caps. In certain embodiments, the implant includes 6 orthogonally arranged arms, each arm having an end cap. In some embodiments each end cap is integrally formed with its respective arm, while in other embodiments each end cap is attached to its respective arm. In other embodiments, the device includes at least one arm that is adjustable in length.

In some embodiments, the application of external beam radiation is used to treat the tissue surrounding the cavity.

In certain embodiments, the bioabsorbable implant is sized to substantially fill the tissue cavity.

Certain embodiments provide an implant that substantially maintains its predetermined shape for a period of about at least six weeks.

In other embodiments, the diameter of the bioabsorbable implant is approximately 2 to 5 centimeters.

In some other embodiments, the implant has a two to four month absorption time.

Certain embodiments provide a means for visualizing the implant by manufacturing the implant from a material having a Hounsfield number between about 60 and 100.

Alternatively, the means for visualizing is provided by manufacturing the implant from a material having a Hounsfield number between about −140 and 50.

In a further aspect of the invention, a method for targeting and delivering therapeutic rays to a patient's soft tissue is provided. This method includes imaging an implanted device within soft tissue in the patient where the implanted device is substantially rigid, has a predetermined shape, and has a means for being imaged. A region of target tissue surrounding the implanted device is then determined, a radiation dose from a source external to the patient is targeted to the target tissue, and the targeted radiation dose is delivered. In some embodiments, the invention may be deformable under external loads and at least partially recoverable when the load is removed, thereby providing an overall volumetric shape around which to target a therapeutic external radiation source or sources.

In certain other embodiments, the process of imaging the implanted device, determining a region of target tissue, targeting an energy source to the target tissue, and delivering the targeted energy is repeated over time without removing the implanted device or acting to alter its configuration.

In further embodiments, each of the embodiments discussed above for implants with respect to the first aspect of the invention can also be applied to the implanted device of this aspect of the invention.

In a still further aspect of the invention, a system for targeting energy sources to target tissue surrounding a tumor resection cavity is provided. The system includes an implantable device having a body that is substantially rigid and has a predetermined shape which also may contain identifiable and orienting features. The body is further bioabsorbable and either is, or is filled with, a material having a Hounsfield number (or an MRI or ultrasound property) that is different from that of the surrounding tissue so that the device can be imaged. When the appropriately sized device is placed in a resected cavity surrounded by soft tissue, it causes the cavity to conform to the predetermined shape. The implantable device is further imageable due to its interior density being less than that of soft tissue such that the boundaries of the tissue corresponding to the predetermined shape can be determined.

In certain embodiments, the body of the implantable device includes a plurality of arms emanating from a center of the implant. The arms have end caps contacting tissue around the cavity to maintain a desired shape of the cavity while still allowing seroma to pass through between the end caps. The end caps are integrally formed with their respective arms in some embodiments, while in other embodiments the end caps are attached to their respective arms. Certain embodiments also include at least one arm that is adjustable in length.

In other embodiments, the body of the implantable device includes 6 orthogonally arranged arms, each arm having an end cap.

In another embodiment, the means for being imaged is provided by manufacturing the implant from a material having a Hounsfield number below about 50.

Other embodiments provide the means for being imaged by manufacturing the implant from a material having a Hounsfield number between about −140 and 50.

In further embodiments, each of the embodiments discussed above for implants and implanted devices with respect to the first and second aspects of the invention can also be applied to the implantable device having a body of this aspect of the invention.

In a fourth aspect of the invention, a method of identifying a lumpectomy cavity in the breast is provided. The method includes performing a lumpectomy, then placing a bioabsorbable device in the cavity. The bioabsorbable device has orthogonal arms emanating from its center and each arm contains radiopaque directionally orienting elements at its periphery. The device is placed in the cavity in a specific anatomical orientation that correlates to the position of the peripheral marking elements. Further, the device allows the lumpectomy cavity wall to partially encapsulate the peripheral marking elements. The lumpectomy cavity is then closed.

In another embodiment, the method includes using the bioabsorbable device to guide re-excision when pathology indicates a need for further tissue excision.

In further embodiments, each of the embodiments discussed above for implants, implanted devices, and implantable devices having a body with respect to the first, second, and third aspects of the invention can also be applied to the bioabsorbable device of this aspect of the invention.

BRIEF DESCRIPTION OF THE DRAWINGS

The invention will be more fully understood from the following detailed description taken in conjunction with the accompanying drawings.

DETAILED DESCRIPTION

The invention described herein uses implantable devices that can allow for more accurate targeting of external beam radiation to the region of tissue that is to be treated. The devices provide a reproducibly-shaped 3-dimensional target that is used to focus the radiation therapy treatment beams directly onto the targeted tissue—for example, the tissue surrounding a resected tumor cavity. The device may be formed of an absorbable material that is implanted at the time of tumor resection and requires no second procedure to remove (it dissolves in situ in the patient's body).

Figure 1:
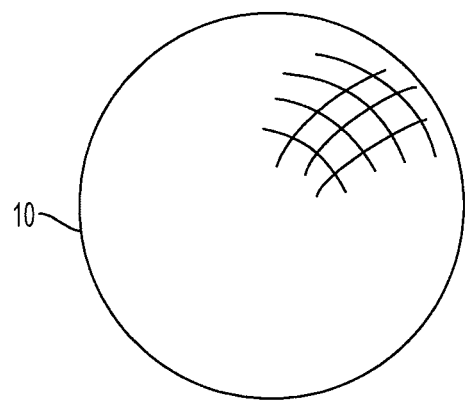
FIG. 1 illustrates an implantable device of the invention.

In one embodiment, the invention includes a bioabsorbable surgical implant 10 (illustrated in FIG. 1 in a spherical configuration) with at least one integral radiographic (or ultrasonic or MRI) visualization (targeting) property. The device can have sizes ranging from 5 mm in diameter to 5 cm in diameter (other sizes are possible depending upon the application). Preferably, the implant 10 has a predetermined shape that can facilitate easy and simple treatment beam profiles, such as spheres, ellipsoids, parallelepipeds (e.g., rectangular boxes). In this way, the implant can be visualized, and its contours (and thus the contours of the target tissue to be treated—typically marginal regions surrounding an excised tumor) readily determinable. Treatment can then be applied to the target tissue. The size and shape of the implant can be varied to correspond to the most common resection cavity sizes and shapes. The device may be in its predetermined shape before placement or may assume that shape upon mechanical manipulation or following implantation (e.g., it may be evacuated such that upon contact with air or fluids it absorbs the air or fluids and returns to its intended shape).

The implant 10 may have one or more of the following key features:

1) Integrated targeting feature (allowing radiographic, magnetic resonance, or ultrasonic visualization) of the tissue/cavity region displaced by the device;

2) Multiple sizes of implant, each having a relatively fixed shape upon implantation;

3) Bioabsorption over a specified or desired time period;

4) Isocenter and/or peripheral border imaging capability; and

5) The device/implant can be inserted at the time of surgical resection of the tumor or as a minimally invasive procedure at some time period following biopsy and/or surgery.

Figure 2:
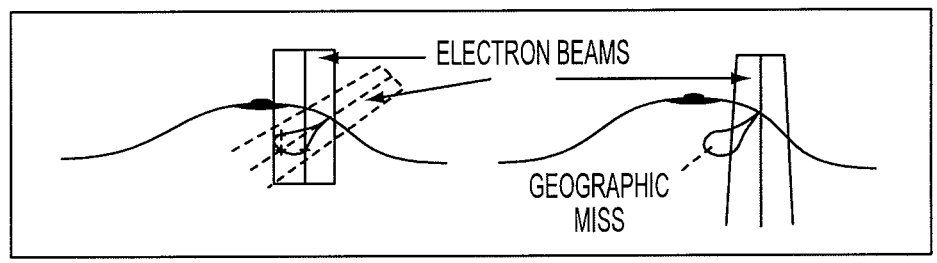
FIG. 2 illustrates the targeting and delivery of therapeutic rays as it is known in the prior art.

It is important that the implanted targeting device 10 be visible on radiographs (MV and/or KV x-rays), ultrasound equipment, and magnetic resonance imaging equipment. FIG. 2 illustrates how this imaging capability is important. On the left, two electron beams are properly targeted onto a lumpectomy cavity and its margin. On the right a single electron beam, using only the skin scar as its target, misses much of the cavity and its margin. The accurate targeting on the left is the result of being able to visualize the target for every fraction and adjust the beams (or the target's location) to make certain the target is adequately covered by the electron beam flux. The inaccurate targeting on the right is the result of using movable or deformable anatomical landmarks (e.g., surgical clips or the lumpectomy scar) to delineate the target.

One reason for inaccurate targeting of the tissue to be irradiated is the inability of one or two points (e.g. fiducial markers) to adequately define the 3-dimensional volume of the target tissue region. Inaccurate targeting is also suboptimal when the markers used to define the target are located at remote locations from the target tissue, as in the case of bony anatomical landmarks and markers or ink markings placed on the skin surface.

While a number of methods, devices, and materials are known to provide radiographic marking, in a preferred embodiment, the implant 10 can have "negative contrast" (a density or, more precisely, a Hounsfield number value less than that of soft tissue), which provides radiographic and, in some cases, ultrasonic contrast to facilitate visualization on these imaging modalities. Ultrasound visualization may also be accomplished when the interior or exterior of the device has different echogenic properties from those of the tissue or cavity borders surrounding it. Other properties may be beneficial for these and other imaging modalities. For example, stainless steel, titanium markers, or other high density material or metal may be placed at the isocenter of the device or at various peripheral regions for enhanced targeting ability that is visible and compatible for x-ray and magnetic resonance imaging. Constructing the device with physical properties that allow on-board imaging systems to "see" the target provides the means to reposition the patient and/or to alter the treatment beams to ensure optimal targeting. This targeting can be used for every fraction delivered to the patient.

Preferably, the implant 10 is completely bioabsorbable, though other configurations with at least portions of the implant being non-resorbable may be desirable. One example is the incorporation of one or more wireless transponders that provide wireless signals that can be interpreted as to the 3-D location (in the Linac's frame of reference) of the transponders. Calypso Medical's Beacon Transponder™ is an implantable transponder that provides localization data for targeting purposes. The Calypso transponder is a fiducial marker whose position is established by radio signal triangulation rather than imaging (i.e., no imaging is performed at all). Thus, the transponder itself is not an image guided localization device. There are numerous ways to alter bioabsorbable materials to achieve the desired imaging capability. One way is to incorporate air or gas pockets, bubbles or other voids in the resorbable material. Another way is to make the implant 10 hollow and filled with air or another material that provides the desired negative contrast.

Various materials that could be used to construct such an implant include known biosorbable materials such as polyglycolic acid (PGA, e.g., Dexon, Davis & Geck); polyglactin material (Vicryl, Ethicon); poliglecaprone (Monocryl, Ethicon); and synthetic absorbable lactomer 9-1 (Polysorb, United States Surgical Corporation). Other materials include moldable bioabsorbable materials such as polylactic acid (PLLA) and PLLA/PGA blends. These blends include caprolactone, DL lactide, L lactide, glycolide and various copolymers or blends thereof. Other foamable materials that can be utilized in the present invention include, without limitation, proteins such as collagen, fibronectin, laminin and fibrin, most preferably collagen, and high molecular weight polysaccharides, such as heparan sulphate, chondroitin sulphate, hylauronic acid and dermatan sulphate. Mixtures of any of the aforementioned materials also can be used, as required. The materials can be modified, by cross-linking, surface texturing, or blended with one another to control degradation rates over varying lengths of time, after which they are substantially or completely resorbed.

In one preferred embodiment, the device has multiple layers of bioabsorbable materials. For example, the core of the largely spherical device is filled with collagen (in one of its many physical forms) and is surrounded by a layer of other, stiffer or more resilient bioabsorbable materials such as Vicryl or Monacryl. The Vicryl or Monacryl material can be laid down as a sheet or as a thread. Alternatively, the outer layer may be a continuous shell or a discontinuous (e.g., geodesic) structure made of molded PLLA or PLLA/PGA blend. This layer of tougher material produces the material strength of the device to maintain a specific shape (e.g., a sphere) and an optional internal bioabsorbable material (e.g., collagen) may serve as a filler. The outer material may govern the overall rate of resorption and may include a semi-permeable membrane or as a temporarily impermeable membrane.

In certain embodiments, the material used to form an implant can be characterized by its Hounsfield number (also referred to herein as "H-number"). The Hounsfield unit scale is a linear transformation of the original linear attenuation coefficient measurement to one in which the radiodensity of distilled water at standard pressure and temperature is defined to have a Hounsfield number of zero, while the radiodensity of air at STP is defined to have a Hounsfield number of −1000. For a material X with linear attenuation coefficient $\mu X$, the corresponding HU value is therefore given by $$\frac{\mu_X - \mu_{H_2O}}{\mu_{H_2O}} \times 1000$$

where $\mu_{H2O}$ is the linear attenuation coefficient of water. Thus, a change of one Hounsfield unit represents a change of 0.1% of the attenuation coefficient of water since the attenuation coefficient of air is nearly zero. Hounsfield numbers for common substances include:

| Substance | HU |
| --- | --- |
| Air | −1000 |
| Fat | −120 |
| Water | 0 |
| Muscle | +40 |
| Contrast | +130 |
| Bone | +400 or more |

Breast tissue, which includes glandular, fat and fibrous tissues, has a range of H-numbers generally in the range of −140 to 50. Fibrous and glandular tissues are typically at the higher end of this range.

In one embodiment where the structure of the implant itself provides the negative contrast imaging feature for X-ray visualization, the Hounsfield number of the implant material in device 10 should be less than +50. It may be substantially lower (less than or equal to about −140), slightly lower (between about 0 and 50) or intermediately lower (between about −140 and 0) than the Hounsfield number of the adjacent soft tissue (e.g., breast tissue). It may also be desirable to construct an implant with portions that are made of materials with a density higher than that of soft tissue to enhance visibility on KV or MV x-rays. The density should not be so high as to impart clinically significant attenuation of the radiation beams or imaging artifact, which may result in clinically compromised target delineation or altering the dose delivered by a clinically significant amount. For these higher H-number embodiments, the higher H-number material does not need to be uniformly spread throughout the device. Rather, a portion of the outer aspect of the device may have higher H-numbers (contrast) with the inner aspect having lower H-numbers. For example, in a spherical or ellipsoid embodiment, the outermost few millimeters of material may be impregnated with x-ray visible media (e.g., barium sulfate, Iohexol™, Omnipaque™ or other biocompatible high density matter), while inside this shell, the device would be made of any bioabsorbable material of lower Hounsfield number (lower than the surrounding tissue).

In one embodiment that is useful for certain treatments of breast tissue, it is desirable for the marker device to have a Hounsfield number in the range of about 60 to 100 (about, in this case, meaning within 10 units). For electron and proton beam treatments, it can be helpful for the device to have attenuation characteristics that are similar to breast and muscle tissue to prevent the over or under attenuation of the beams (for which there may not be a ready compensation). A Hounsfield number in this range is sufficiently differentiated from breast tissue so as to be imageable, but is within the "normal" range for the treatment instruments.

The material for implant 10 should be rigid enough to provide a fixed and predetermined shape in situ. A fixed and predetermined shape can be a significant advantage in that it provides a standard shape for targeting. In deformable tissues (e.g. breast, lung), the ability of the implant to remodel the surrounding surgical margins into a specific shape (e.g. a sphere, ellipsoid) allows the clinical target volume and planning target volumes (i.e., the target for radiotherapy) to also assume this shape. For resected breast cancer cases (e.g. lumpectomy), the resection cavity often has a relatively irregular shape, and the shape can change day-to-day and even during different portions of the respiratory cycle. Also, the cavity can grow or shrink over the time period (e.g. days or weeks) during which radiation therapy is delivered. Having the target volume in the same shape every day of therapy increases the probability of always hitting the target and reduces the chance of a "geographic miss". A simple shape such as a sphere is one of the easiest shapes for devices such as linacs to sculpt to, both from the treatment planning standpoint (via dose planning software) as well as from a dose delivery standpoint (via the multi-leaf collimator or compensator). Thus, shaping the treatment field is substantially easier and faster for the physicist or clinician to plan and implement. The desired shapes are ones in which the external surface(s) is(are) convex rather than concave. The convex nature of these shapes makes them easier to deliver the appropriate dose while minimizing unwanted dose to adjacent structures.

The sizes of the implant are most preferably in the 1-6 cm diameter range (diameter of the major axis). Other sizes may be preferable, depending on the patient's anatomy and anatomical location of the target. For breast, the diameter range of 2-5 cm is preferred.

The implant should take a relatively rigid configuration in vivo. This will allow the implant to better conform the surrounding tissue to its shape. Rigidity is also beneficial in that the shape of the implant will remain the same for each radiation therapy fraction. It is not necessary for the implant to be completely rigid until resorbed. In some embodiments, the implant may be resiliently deformable, i.e., one that deforms under moderate external compressive or tensile force but may return at least in part to its desired shape upon release from the externally applied force. For example, the breast implant may deform to an ovoid shape (e.g., a tennis ball being pressed between two hands) when the patient is wearing a bra or is prone, but returns to spherical shape when the bra is removed and the patient is supine. As used herein, the term "substantially rigid" refers to the preferred situation in which the implant reproducibly provides a desired shape to the tissue surrounding a tumor resection cavity while allowing some compliance and conformability for the purpose of providing implantation through a smaller incision and/or to provide increased comfort or minimized tissue damage or necrosis for the patient.

The most desirable rate of resorption for bioabsorbable implants will depend on the specific application and anatomic location. In many cases, it is desired that the implant maintain its size, shape, and imaging capacity until radiation therapy is complete Those experienced in radiation therapy will realize this spans a wide range of time intervals. For patients who will move swiftly to radiation therapy, and receive a hypofractionated (accelerated) radiation therapy, the resorption can start as early as 3 weeks post implant. For others, the radiation therapy may not start for several months post surgically (due to, for example, chemotherapy regimens) and radiation therapy may last 7 weeks, thus requiring an implant that remains fully functional for as long as 6 months. In other cases, such as where radiation therapy is not used, the absorption time may be 2-4 weeks as well.

The rate of resorption can be controlled by the manufacturing techniques used to produce the bioabsorbable material. Alternatively, the inner material may be a substance that resorbs fairly quickly when in contact with bodily fluids or tissue, but is surrounded by a more slowly resorbing outer region (thus governing the rate of the implants absorption). Various configurations and materials are also described in U.S. Pat. No. 6,638,308 to Corbitt Jr. et al, which is hereby incorporated by reference. The rate of bioabsorption may also be dictated by the rate at which tissue in-growth may occur.

Regardless of the rate of resorption, having a device that is bioabsorbable is beneficial in that it eliminates the need for a second medical procedure to remove the device from the patient.

The implant may be inserted upon completion of the tumor resection, but prior to closing of the surgical wounds. If implanted in this fashion, one embodiment of the invention is a preformed bioabsorbable implant having the desired size and shape, without need for the surgeon to alter it in any fashion prior to implant. Alternatively, the implant may be adjustable in terms of size or shape by the surgeon using surgical instruments readily available in most operating rooms (e.g., scissors), or by a special tool supplied with the implant (e.g., hemi-spherical cutting tool that rounds the edges of the implant as it is resized. In other embodiments, the implant may be manually altered in size and/or shape without the use of tools (e.g., telescoping articulations).

Figure 3:
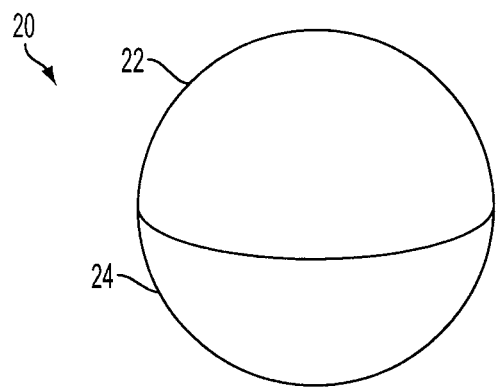
FIG. 3 illustrates an implantable device of the invention having two halves.
Figure 4A:
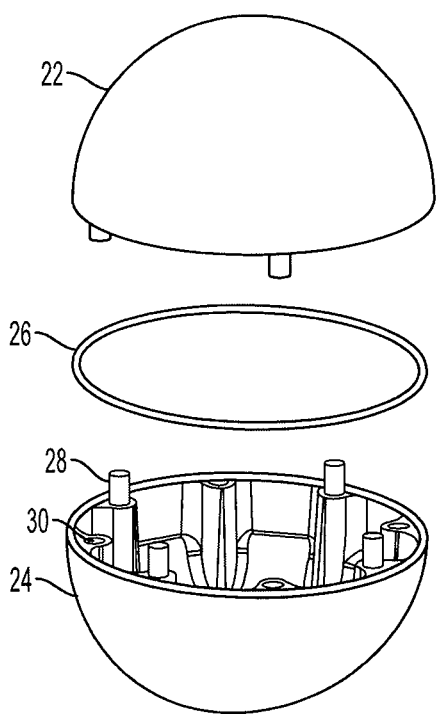
FIGS. 4A-F illustrate an embodiment of the invention having two halves.
Figure 4B:
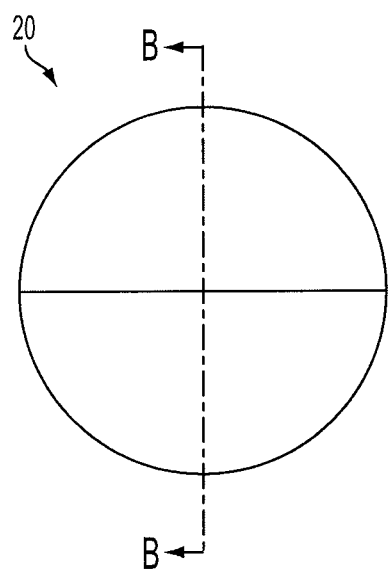
Figure 4C:
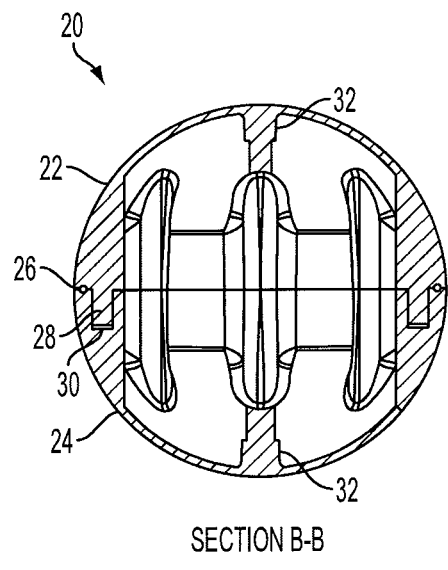

FIG. 3 illustrates a preferred embodiment of the invention in which a hollow bio-absorbable implant 20 is provided in first 22 and second 24 pieces. FIG. 4A shows the implant of FIG. 3 in exploded view, while FIGS. 4B and 4C illustrate the implant in section. In these views, it can be seen that each half 22, 24 is hollow, and that each includes a series of posts 28 and complementary recesses 30 that aid in aligning the halves and holding the implant together. Also, a soft compliant bioabsorbable O-ring 26 can be provided between the two mating equators to create a fluid tight seal. This can be especially beneficial when air inside the hollow implant is used for targeting. In this embodiment, the implant is spherical and the two halves are substantially identical, though this need not be the case.

Figure 4D:
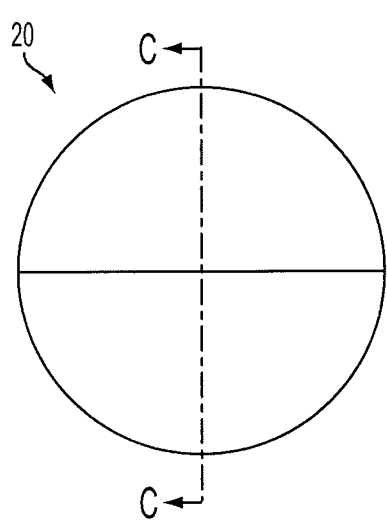
Figure 4E:
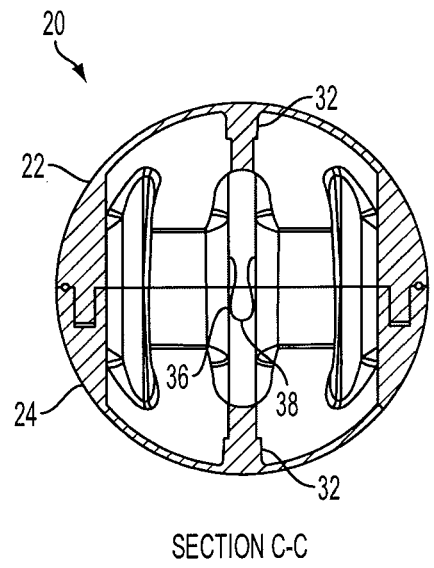
Figure 4F:
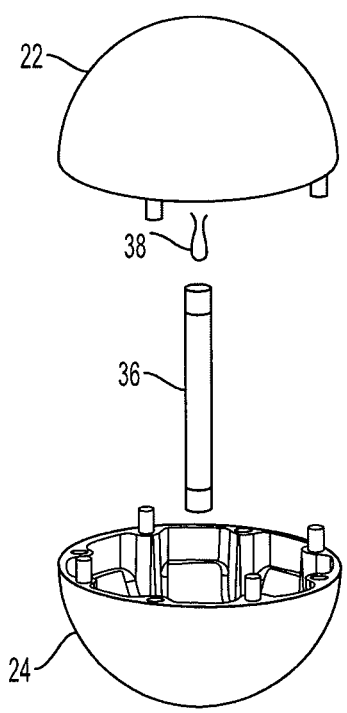
Figure 5A:
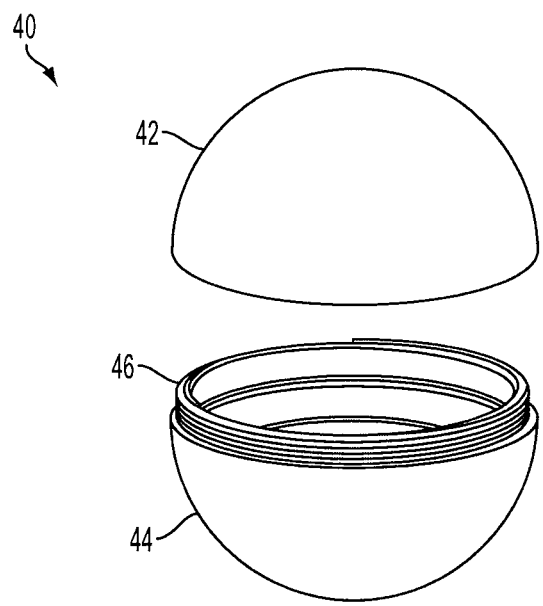
FIGS. 5A-E illustrate a further embodiment of the invention having two halves.
Figure 5B:
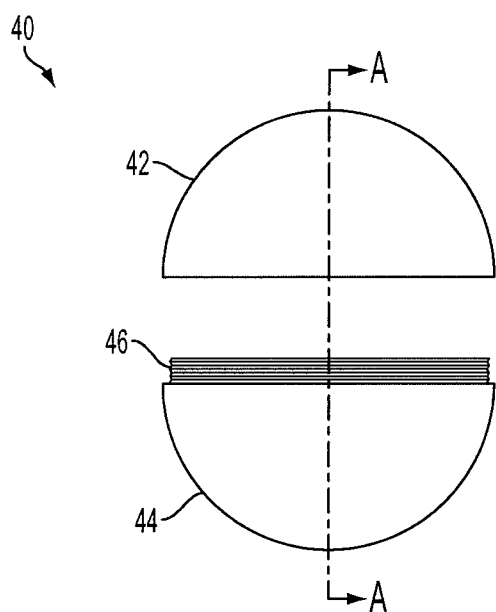
Figure 5C:
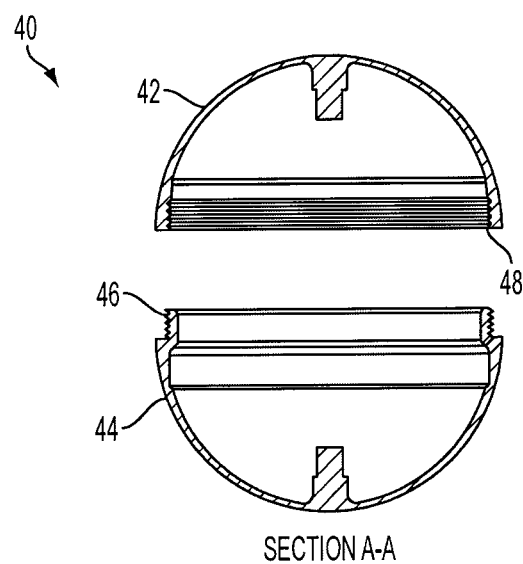
Figure 5D:
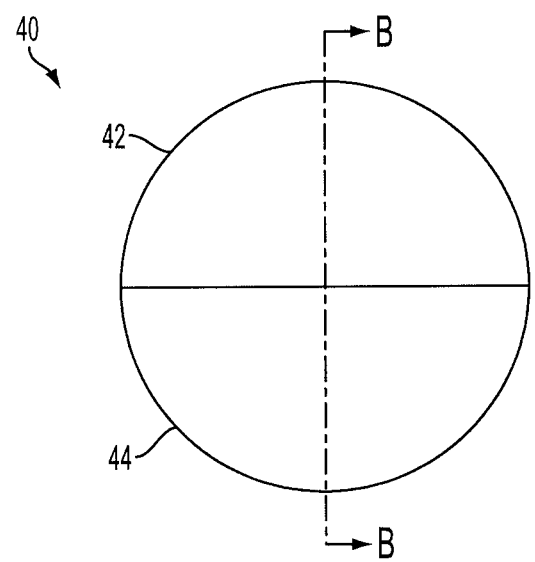
Figure 5E:
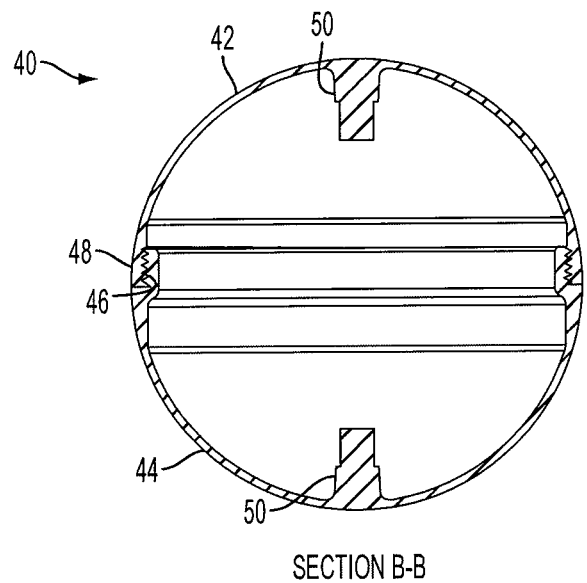

FIGS. 4D, 4E, and 4F (an exploded view without O-ring 26) further illustrate implant 20 having a bio-absorbable tube 36 mounted onto central posts 32 on each implant half 22, 24. Tube 36 can help to hold the two halves together, however, it may also be used to support imaging element 38. In this case, imaging element 38 is a surgical clip or other implantable grade x-ray visible bio-compatible material (such as stainless steel or titanium). The imaging element 38 is also located at the geometric center of the implant 20. In this way, by knowing the geometry of the implant (a sphere of a given radius in this example), and knowing the location of the geometric center of the implant (determinable from the imaged location of the imaging element 38), the location of the implant surface (and thus the surface of the tissue surrounding the implant) can be determined, or corroborated with other measurements. Also, the centrally located imaging element can serve as the isocenter for the target, a useful term for tracking the location of the target tissue. As an alternative to a separate tube 36, an integral material segment (not shown) may extend from the internal surface of the hemisphere to create a hollow region at the geometric center of the device for the imaging element 38 to reside.

Because implant 20 can rely on its hollow interior and/or imaging element 38 for imaging purposes, the materials used to form the implant can be selected for manufacturability (i.e., extrusion, injection molding) and desired bio-absorption characteristics rather than imaging properties. In a preferred embodiment, the implant is formed from a blend and/or copolymer of PGA and PLLA and/or polycaprolactone (CPA). PGA, used as an acronym for polyglycolide or polyglycolic acid, is a biodegradable, thermoplastic polymer and the simplest linear, aliphatic polyester. It can be prepared starting from glycolic acid by means of polycondensation or ring-opening polymerization. Studies performed with polyglycolide sutures have shown that the material loses half of its strength after two weeks and 100% after four weeks—the polymer being completely resorbed by the organism in a time frame of four to six months. PLLA, an acronym for polylactides or polylactic acid, is another bioabsorbable thermoplastic aliphatic polyester. PLA may exist in a variety of forms including poly L lactide, poly D lactide and a copolymer of the two, called poly DL lactides. CPA, used as an acronym for polycaprolactone, is another bioabsorbable polymer that is ductile under loads. All of the above-mentioned bioabsorbable polymers may be blended or copolymerized with one another or used as components of the device to achieve a variety of different mechanical properties and absorption rates. Some material blends that may have a particularly desirable range of mechanical properties and absorption times include 100% PGA, a 50/50 molar ratio of DL lactide and polyglycolide, and a 70/30 molar ratio of L lactide and CPA. These materials may achieve a 2 to 4 month absorption time with good strength before absorption. Data on commercially available forms of these materials is included in an appendix attached to the provisional version of this application, which is incorporated here by reference.

An implant formed from these materials, or a combination thereof, may not have a negative contrast, and may even be slightly denser than the soft tissue that surrounds it after implantation. As noted above, the structural material of the implant itself may not be visible in situ for imaging purposes—accordingly, the only limitations on the density of the implant material may be that it does not create clinically significant artifacts, or clinically alter (significant attenuation or decreased attenuation) the therapy beam.

A further embodiment of the invention is illustrated in FIGS. 5A to 5E. In those figures, implant 40 is provided having two halves 42, 44. In this embodiment, the two halves are connected using male 46 and female 48 threads on the two halves. Central posts 50 can also be provided to position a tube and centered imaging element as was done in the embodiment above. An O-ring (not shown), similar to that described in FIG. 3, may also be employed to enhance sealing the connection between the two hemispherical shells from external bodily fluids (e.g., seroma).

Figure 6A:
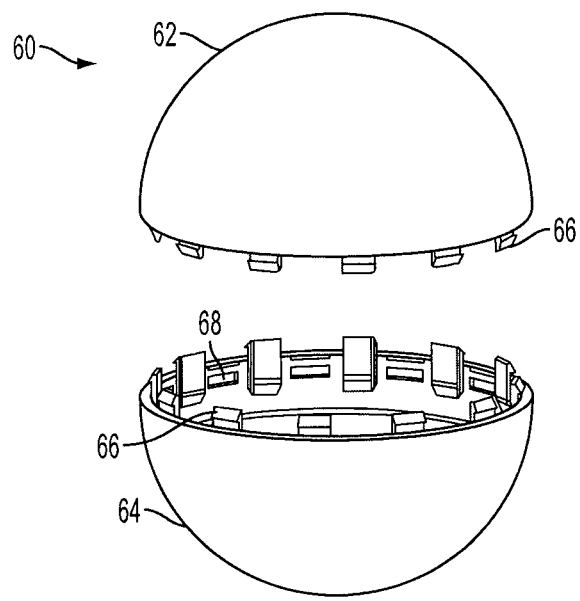
FIGS. 6A-C illustrate a further embodiment of the invention having two halves.
Figure 6B:
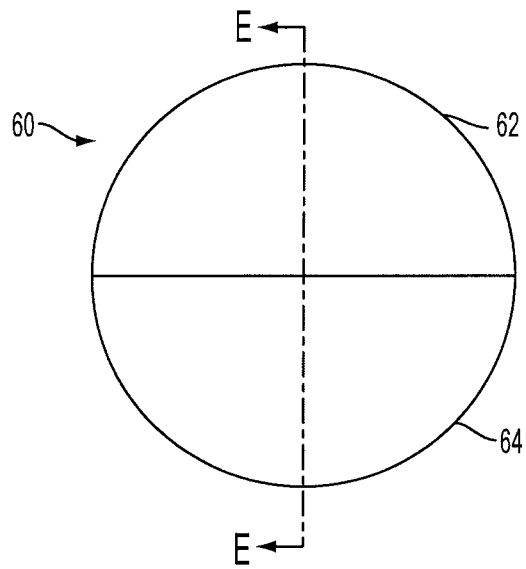
Figure 6C:
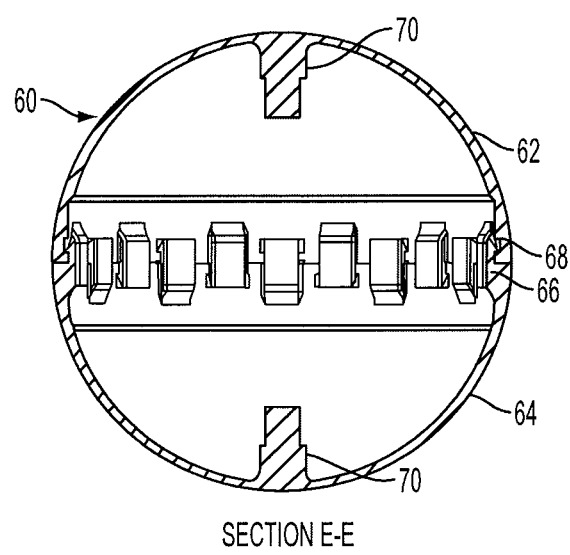

Another embodiment is provided in FIGS. 6A to 6C. In this embodiment, each half 62, 64 of implant 60 includes biased clips 66 that mate with complimentary features 68 on the other half. This embodiment can also have central posts 70 for the reasons explained above.

Figure 7A:
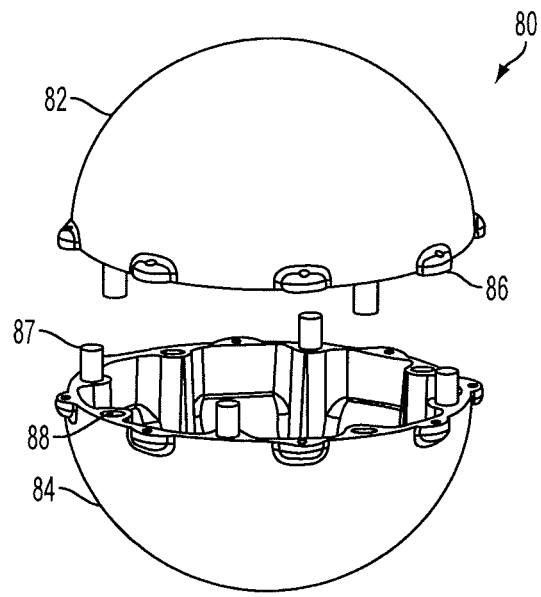
FIGS. 7A-B illustrate a further embodiment of the invention having two halves.
Figure 7B:
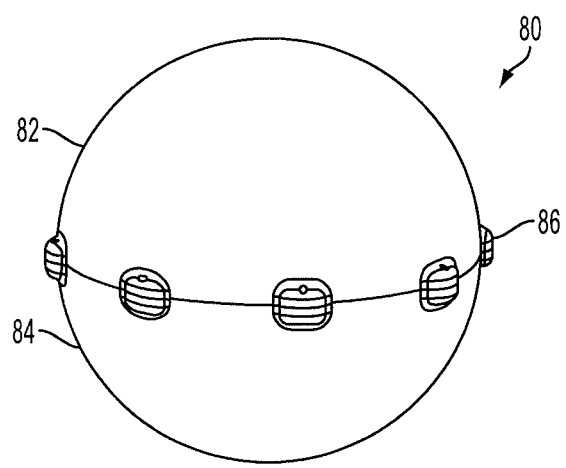

A still further embodiment is illustrated in FIGS. 7A and 7B. In this embodiment, each half 82, 84 of implant 80 includes an external mount 86 that aligns with a complementary mount on the other half when the implant is assembled. A metallic clip (not shown) can be placed around (or through) one or more of the aligned mount pairs to help hold the implant together. Such clips, or the mounts themselves, could include an imageable material. The implant halves 82, 84 can also include protrusions 87 and recesses 88 or other alignment features as are described with respect to FIG. 4 above, for example. In addition, central posts can be provided as shown in other embodiments for the reasons stated above.

Figure 8A:
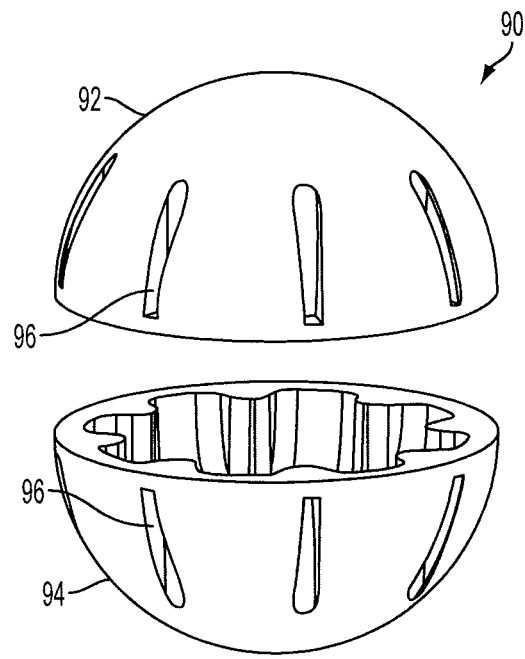
FIGS. 8A-B illustrate a further embodiment of the invention having two halves.
Figure 8B:
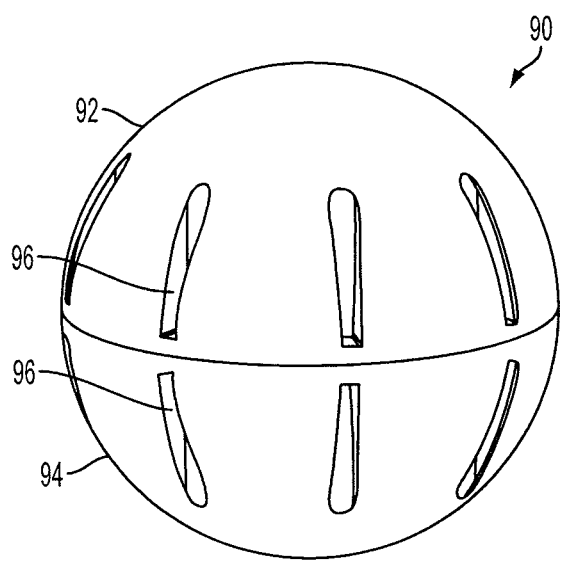

FIGS. 8A and 8B illustrate a further implant 90 having halves 92, 94 that have indents 96 that are aligned when the implant is assembled. The indents allow room for an externally applied welding horn, heat staking element, or sealing device to join the two halves of the implant. An external clip (not shown) can be used to hold the implant together at one or more of the indent pairs. This implant could also be provided with protrusions and recesses, or central posts, as applied above to aid in imaging and/or alignment of the halves.

Figure 9:
FIG. 9 illustrates a resected tumor cavity in soft tissue as is known in the prior art.

A method according to the invention for treating these and other malignancies begins by surgical resection of a tumor site to remove at least a portion of the cancerous tumor and create a resection cavity as illustrated in FIG. 9. As illustrated, an entry site or incision 102 is created in patient 100 in order to remove tissue and create an irregularly shaped cavity 104.

Figure 10:
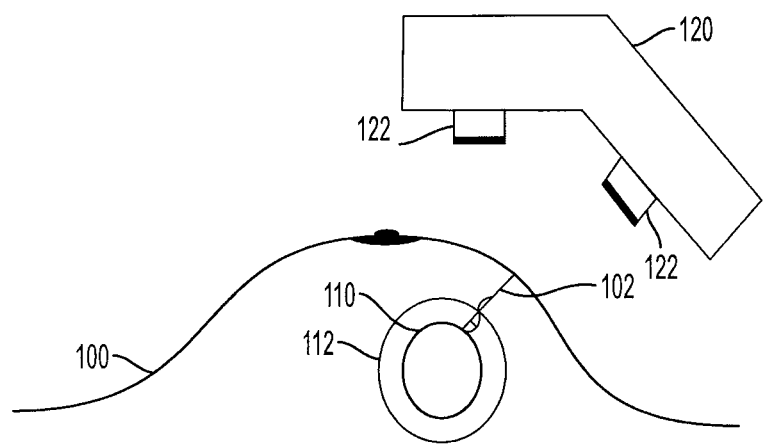
FIG. 10 illustrates the delivery of therapeutic rays according to the invention.
Figure 11A:
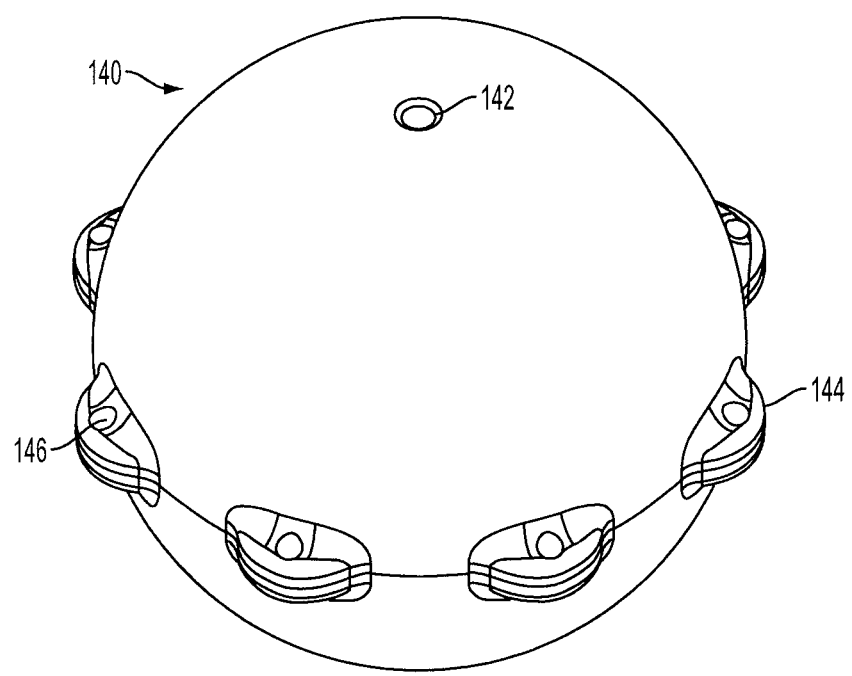
FIGS. 11A-E illustrate a further embodiment of the invention having two halves.
Figure 11B:
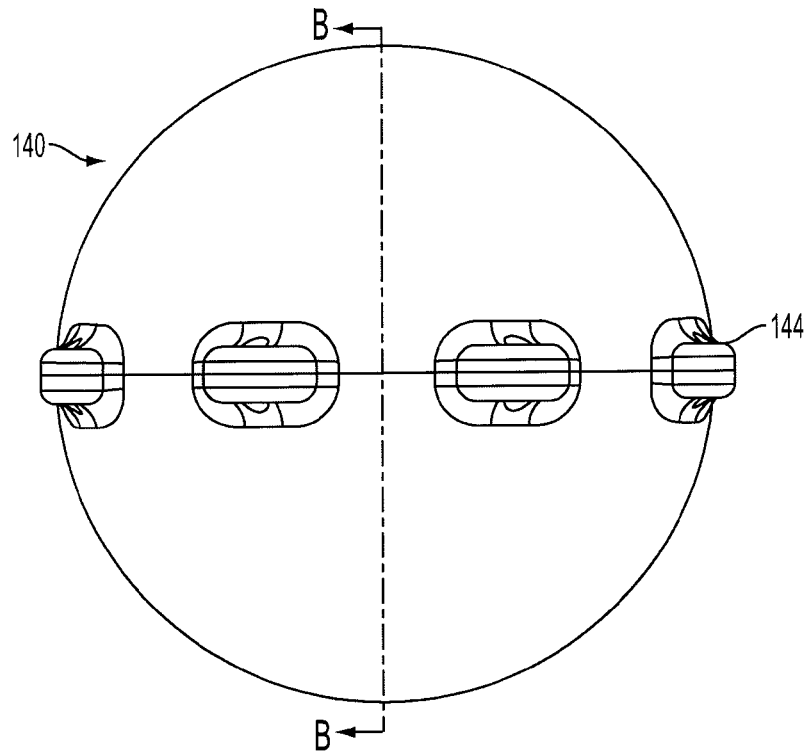
Figure 11C:
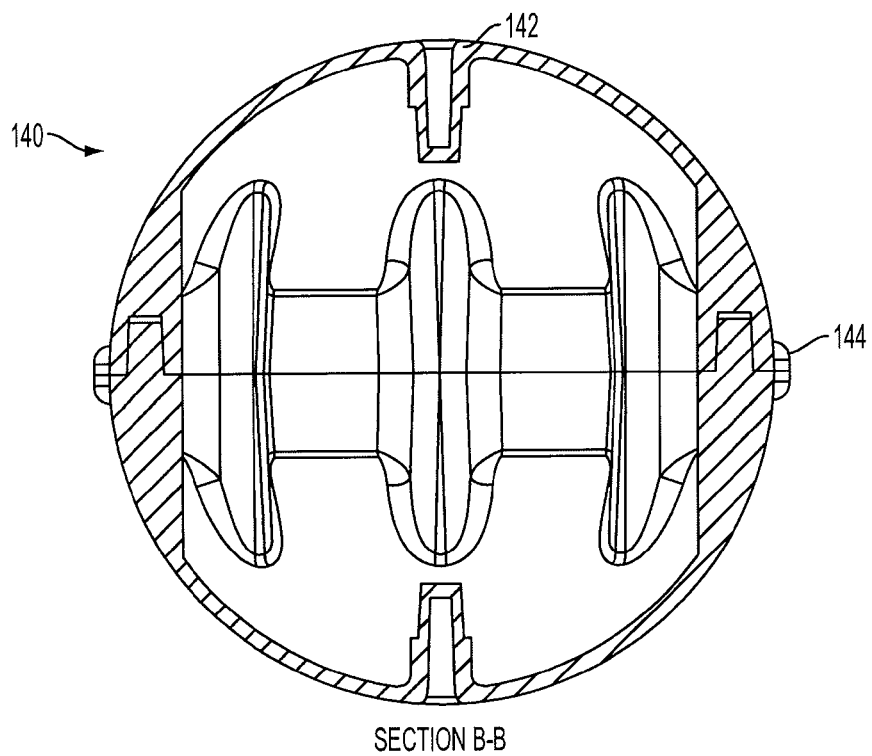
Figure 11D:
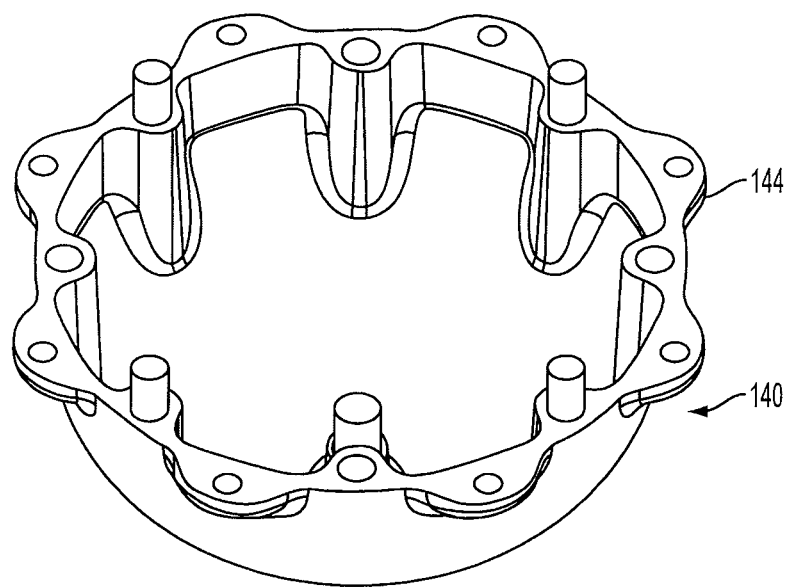
Figure 11E:
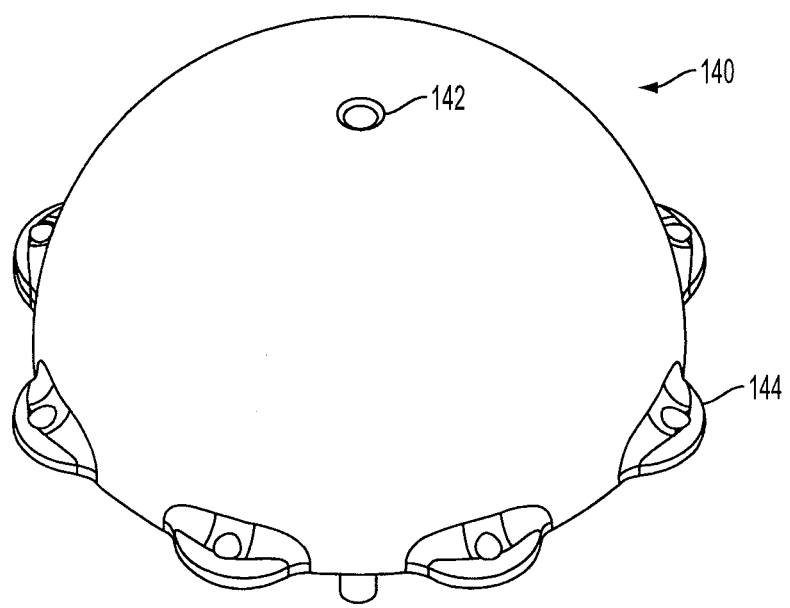

Following tumor resection, as further illustrated in FIG. 10, an implant of the invention (using any of the embodiments described herein) is placed into the tumor resection cavity 104. Placement can occur prior to closing the surgical site 102 such that the surgeon intra-operatively places the device, or alternatively device can be inserted once the patient has sufficiently recovered from the surgery. In the later case, a new incision for introduction of the device may be created. In either case, the surface of the device, which is preferably sized and configured to reproducibly position tissue surrounding the resection cavity 104 in a predetermined geometry, is placed within the resected tissue cavity.

Following insertion of the implant device, such as by an open method or using a mini-open or minimally invasive procedure, the implant occupies the tissue cavity 104 and supports the surrounding target tissue 112 until such time as it resorbs or biodegrades. When the implantable device is implanted in a resected cavity in soft tissue it causes a substantial portion of the cavity to conform to the predetermined shape of the implant. "Substantial portion" is used herein in this context to mean greater than or equal to about 25% of the outer surface of the implant is in direct apposition to the surrounding tissue. Given the irregularities of many lumpectomy cavity shapes, not all of the surface of the implant will be in direct apposition to the surrounding tissue. There may be some voids filled by air or seroma. However, for the implant to be a useful targeting aid, a significant portion should be in contact, e.g., greater than or equal to about 50% of the implant surface. In some embodiments, the implant fully conforms to the surrounding tissue—where fully conforms means greater than or equal to about 95% of the implant surface will be in direct apposition to surrounding tissue.

In many embodiments, the implant is sealed so that, after initial implantation, the patient's own fluids do not penetrate to the interior of the implant until such time as the implant walls degrade due to their bio-absorbability. The implant can be filled, and can be filled with a negative contrast agent (including in some cases being filled with air) for imaging or other purposes.

With the implant device (again, using any of the embodiments described herein) in place, it supports the target tissue 112 surrounding the tissue cavity and reduces tissue shifting. In addition, the surface of the device can position the target tissue 112 in a predetermined geometry. For example, a spherical implant, as illustrated in FIG. 10, can position the target tissue 112 surrounding the tissue cavity 104 in a generally spherical shape. With the target tissue 112 positioned, a defined surface is provided so that radiation can more accurately be delivered to the previously irregular tissue cavity walls. In addition, the device helps reduce error in the treatment procedure introduced by tissue movement. The positioning and stabilization provided by the implant device greatly improves the effectiveness of radiation therapy by facilitating radiation dosing and improving its accuracy. The result is a treatment method which concentrates radiation on target tissue and helps to preserve the surrounding healthy tissue.

Prior to delivering radiation, but after placing the implant device, the device and the surrounding target tissue 112 can preferably be visualized with an imaging device, including by way of non-limiting example, x-ray, ultrasound, MRI, CT scan, PET, SPECT, and combinations thereof. These imaging devices provide a picture of the implant device and the surrounding target tissue 112 to assist with the planning of external radiation therapy. To aid with visualization, the device can use any of the techniques described above to locate the surface of the device. Thus, the device shapes the cavity to a target shape which is more amenable to receiving the radiation therapy beams (as compared to an irregular cavity). The device then provides a target for more accurate repositioning of the patient's targeted tissue immediately prior to each fraction of treatment. Finally, it can provide a means of real-time tracking the motion of the target volume so that the beams can either move with the target or can be turned on and off as the target moves out of and back into the beams' path.

In a preferred embodiment, the imaging modality takes advantage of the implant device having a hollow interior that is filled with air or some other material having a lower density or lower Hounsfield number than the surrounding soft tissue. As explained above, this portion of the implant can preferably have a Hounsfield number of less than or equal to about 40 in order for it to be readily imageable via radiologic imaging. In addition, the imaging modality can rely on the implant having a predetermined shape and size in order to accurately locate the surface of the implant, and thus the inner surface of the target tissue 112.

In the case of external radiation therapies such as three-dimensional conformal radiation therapy (3DCRT) and IMRT, the imaging procedures provide a map of the residual tissue margin and assist with targeting tissue for radiation dosing. The radiation beams are then adapted for delivering a very precise radiation dose to the target tissue. With the implant device positioning the tissue surrounding the resection cavity, there is less danger of the target tissue shifting (within the body) and thus having the planned radiation missing the planning target volume (PTV) and needlessly damaging healthy tissue.

Some treatment regimens require repeated radiation dosing over a course of days or weeks, and the device can be used in those cases to repeatedly position the tissue surrounding the resected tissue cavity. These steps can be repeated as necessary over the course of a treatment regimen. Preferably, the implanted device remains in place without intervention, i.e., without removal or actions to change its configuration, throughout the course of treatment.

Another embodiment of the invention incorporates fiducial markers that provide real-time, wireless information about the device's spatial position relative to the origin of a coordinate system in the treatment room (e.g., the isocenter of the radiation delivery device or the radiation beam's source location). The spatial position data can be used to correct errors in target volume location. For example, by adjusting the patient's body position on the treatment couch and/or altering the radiotherapy beams' shape and direction to correct for the altered PTV position. Preferably, the real-time, wireless feedback allows correction of positioning errors prior to delivery of each fraction of radiation. Fiducial markers can also provide users a more accurate PTV position and thereby allow greater normal tissue sparing and smaller normal tissue margins within the PTV. Preferably, the fiducial markers and their detection systems are radio-opaque markers that are imaged radiographically (e.g., fluoroscopically) or transponders that signal their positions to a receiver system. An exemplary fiducial marker is the Beacon Transponder, made by Calypso Medical Technologies of Seattle, Wash.

Positioning fiducial markers on the device provides an advantage over other placements of such markers (e.g., placement within a tumor). For example, by placing a fiducial marker in or on a known location on the device having a known shape, the position of the implant surface can be precisely determined. In addition, a marker positioned on the outside or at the perimeter of the device can be used to delineate the surrounding target tissue (a.k.a. the PTV). As an additional benefit of having the marker positioned on the device, a separate insertion step is not required for the markers. In the specific embodiments illustrated herein, an imageable element, such as a titanium clip, can be located at the geometric center of the device as an aid in this type of surface determination.

Imageable elements may also be placed at other locations within or near the surface of the device. For example, implant 140 can include imageable elements such as those found at the polar regions 142 or along equator locations 144 as shown in FIG. 11A through E. The polar regions 142 may consist of hollow regions into which a titanium clip or other radiovisible marker, as previously described, may be placed. The perimeter or equatorial locations 144 may contain titanium wire passed through the holes 146 (e.g., a hog ring, shear pin, or cotter pin, not shown), which may also help keep the two hemispheres held securely together when the device is subject to external forces during the period of implantation. The imageable elements may be shaped or sized differently from each other to delineate the device's orientation. For example the polar markers may be of short length, while the peripheral elements may be of a longer length or of different shape (e.g., circular titanium wire of varying sizes). If the device's orientation is detectable via imaging, it may be used to help guide the clinician to more precisely tailor target volumes for therapy. Further, the polar and perimeter features themselves, without additional targeting elements, can be used to determine the device's orientation, especially where the device is formed of a material having a different Hounsfield number than the surrounding tissue as described above.

In additional alternative embodiments, a targeting device 160 may have multiple protrusions 162 provided on the exterior surface of the device, as shown in FIG. 12A through E. The protrusions may aid in preserving the orientation of the device after it is implanted. To that end, the protrusions 162 can bluntly penetrate into the surrounding tissue to minimize rotation and migration within the surrounding tissue. Also, a textured surface of the device may also be used to minimize device rotation and migration. The textured surface may promote tissue ingrowth to minimize movement in a manner similar to the way breast implants are textured to minimize their movement within the breast. Another advantage of texturing the outer surface of the device is that it can accelerate the absorption rate of the implant relative to smooth surfaced devices.

In addition to surface protrusions 162, device 160 may also include equatorial features 144 to assist in holding hemispheres of the device together, hold an imageable element, and/or act as an imageable element. In preferred embodiments, targeting device 160 includes at least 4 protrusions. The protrusions can take a variety of shapes, and in one preferred embodiment are conical or frustroconical having a length of between about 2 and 5 mm. Further, the protrusions 162 may also be configured to hold imageable elements that will aid in determining the orientation of the device 160.

Figure 12A:
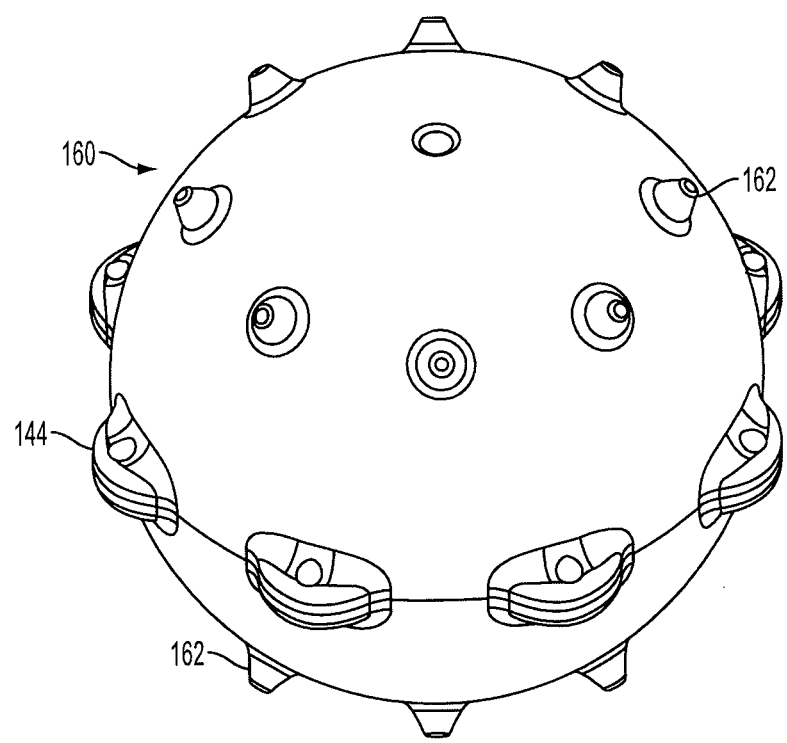
FIGS. 12A-G illustrate two further embodiments of the invention having two halves.
Figure 12B:
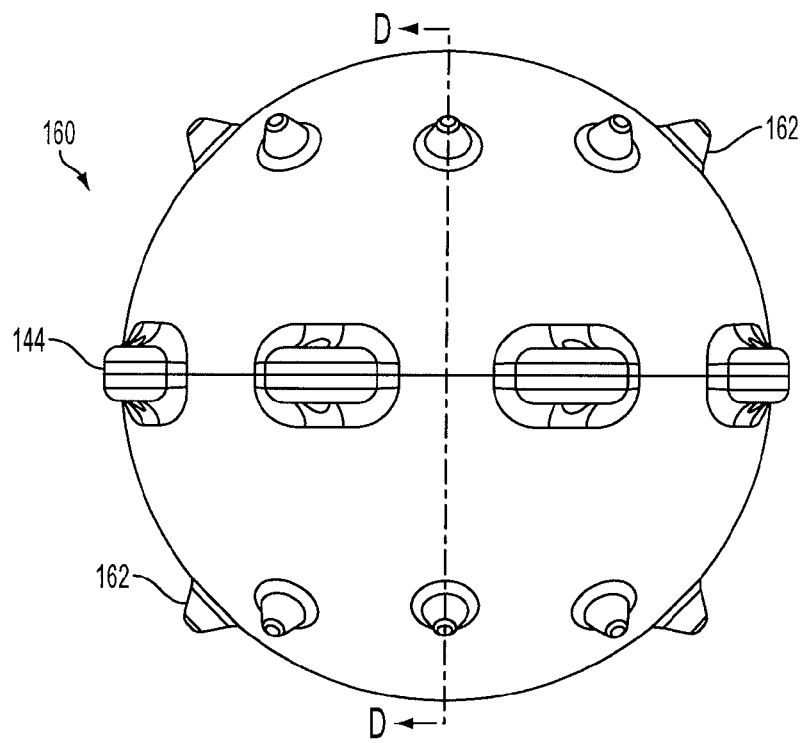
Figure 12C:
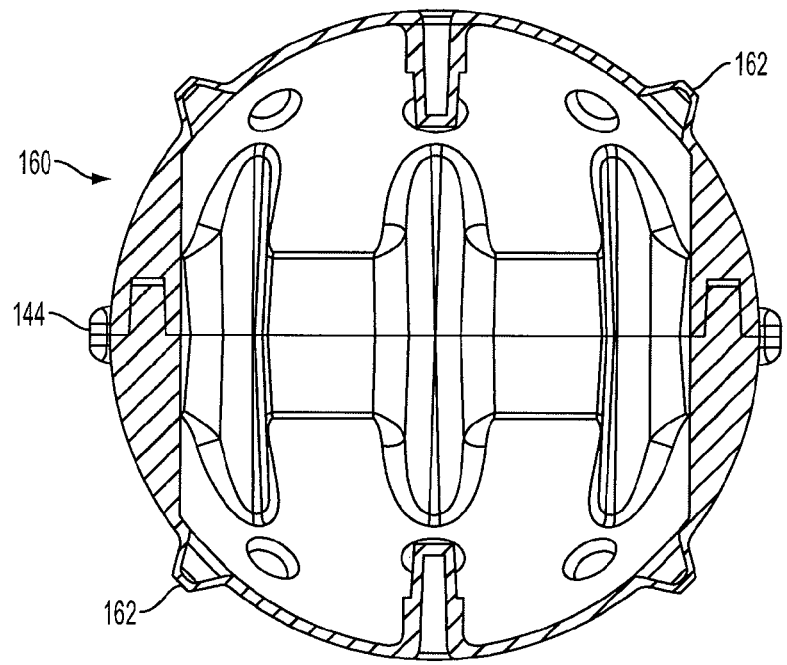
Figure 12D:
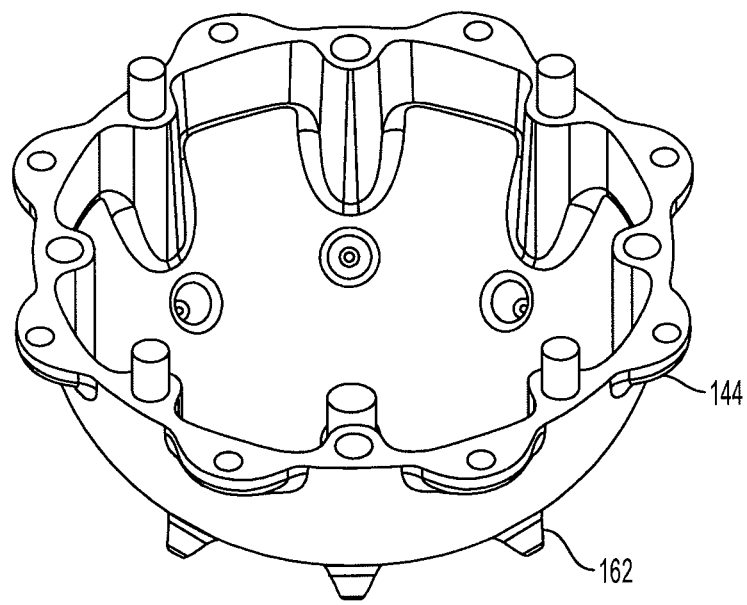
Figure 12E:
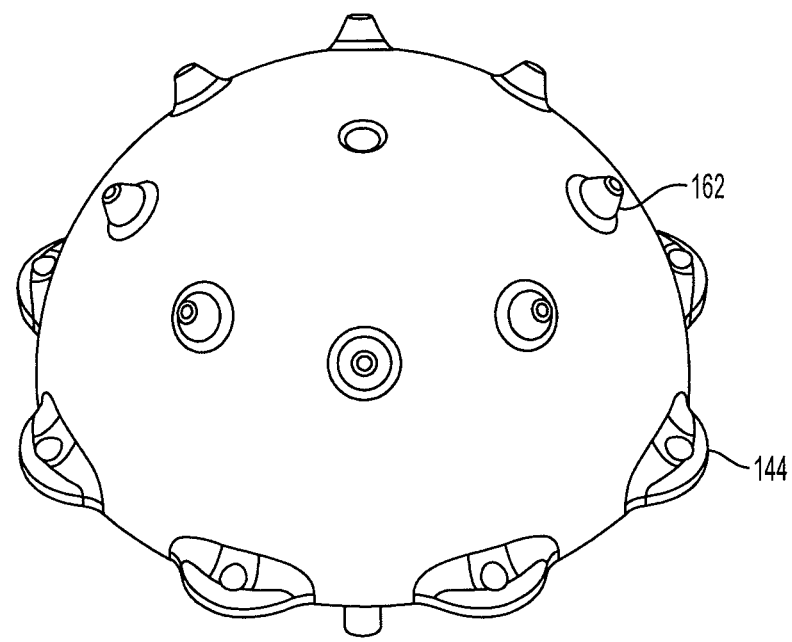
Figure 12F:
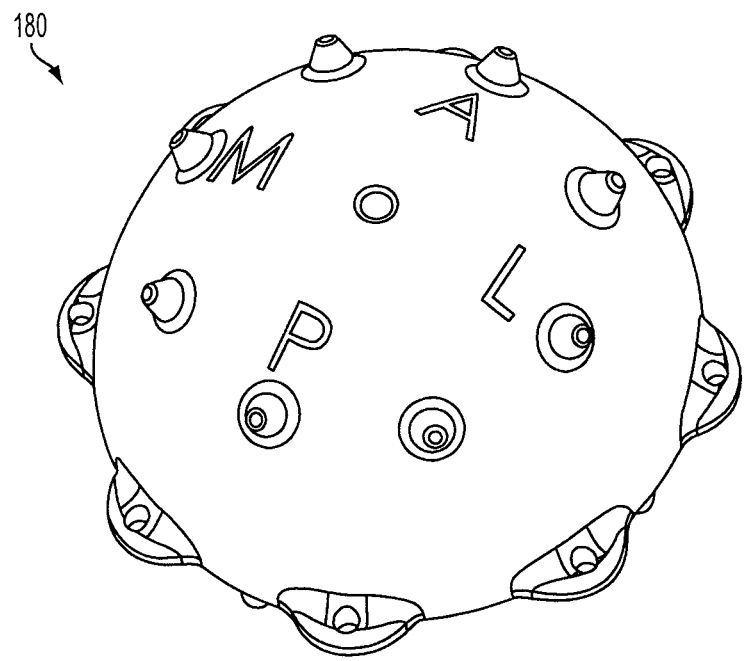
Figure 12G:
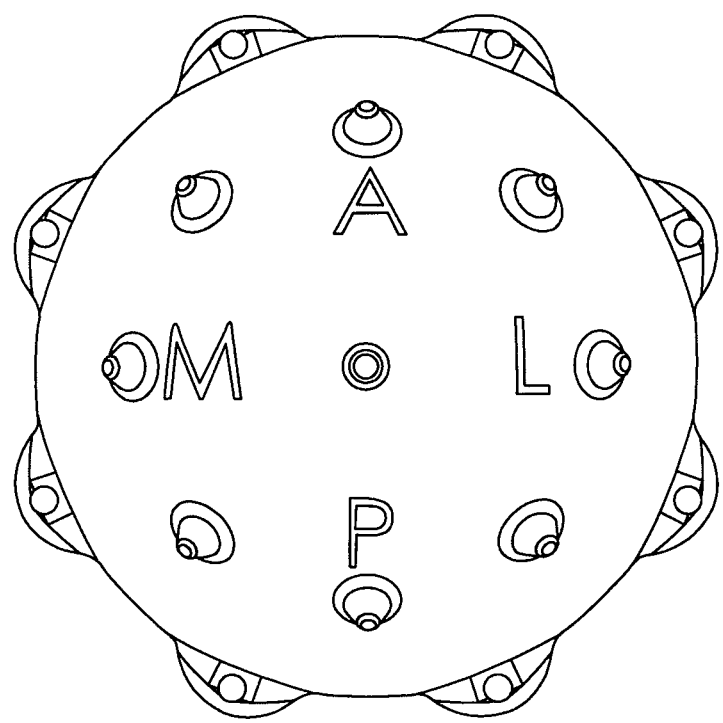

As an additional feature, the device 180, similar to targeting device 160, may be marked with letters to provide direct visual orientation of the device, as shown in FIGS. 12F and 12G. In this embodiment, the surface of the device is embossed or molded with the raised letters A for anterior, P for posterior, M for medial, and L for lateral. In use, the surgeon implants the device after performing the lumpectomy and places the device in a specific orientation that matches the orientation of the patient. After pathology, if additional excision is necessary, the surgeon may use the implanted device as a supplementary indicator of tissue position to guide the exact location of the additional tissue to be removed. For example, if pathology finds dirty margins on the lateral anterior portion of the lumpectomy specimen, the surgeon may use the implanted device with letter markings to ascertain the lateral anterior location of the tissue of the lumpectomy cavity to be excised.

The letters on the surface of the device can be viewed directly by the surgeon. But in addition, regional markers on the device can be used to describe the anterior, posterior, medial, or lateral portions of the device by radiographically visible means. Radiovisible markers of varying size can be placed at various locations (e.g., short marker in the superior region, longer marker in the inferior region, wide marker in the lateral region, and narrow marker in the medial region of the device). With these markers clinicians can, if desired, use the device to guide dose delivery (reduced dose, or enhanced dose) to specific regions of interest at the periphery of the device.

Figure 13:
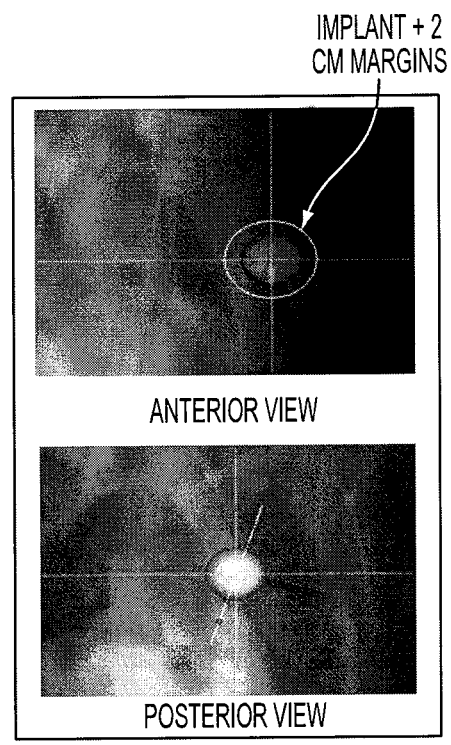
FIG. 13 shows a radiograph with an implanted shaping target device and a treatment margin is shown around the implanted device.
Figure 14:
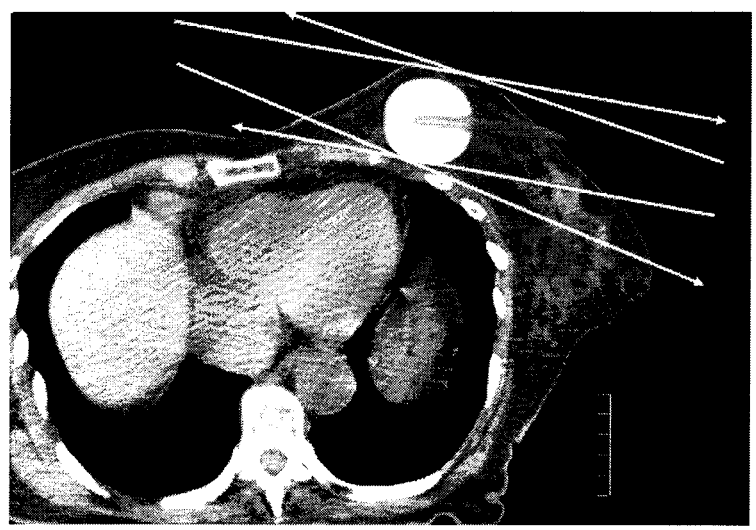
FIG. 14 shows image guided radiotherapy beams intersecting at the implanted device plus margin of FIG. 11.

FIGS. 13 and 14 show radiographs of devices such as those described herein implanted. In FIG. 13, a radiograph shows the implanted shaping target device and a treatment margin around the implanted device. In FIG. 14, image guided radiotherapy beams are shown intersecting at the implanted device and margin of FIG. 13.

Figure 15A:
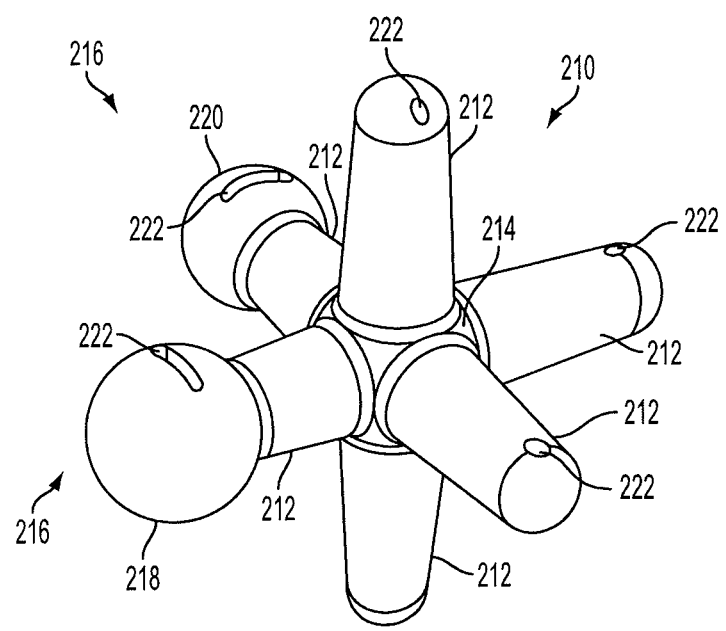
FIGS. 15 A-N show additional embodiments of a marker device with orthogonal radial arms extending from the center of the implant.
Figure 15B:
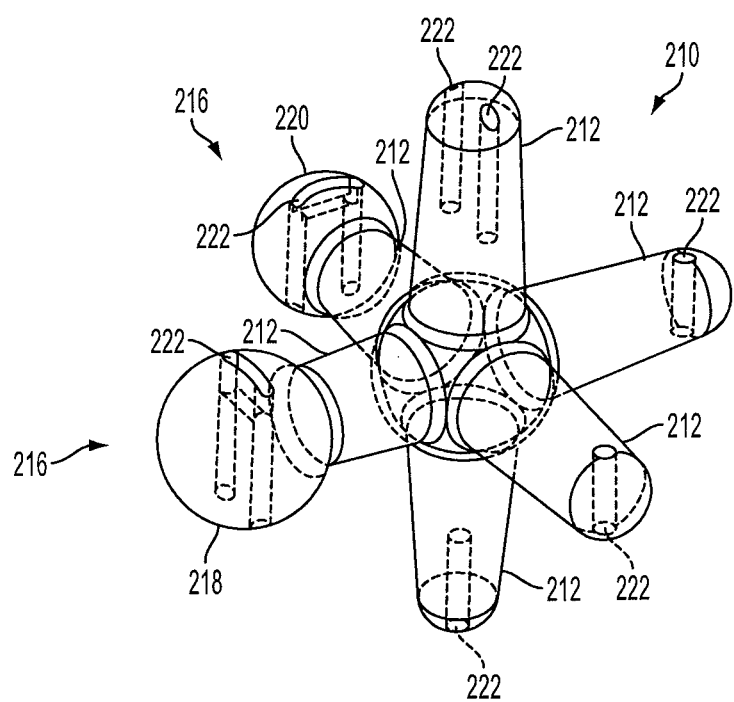

FIGS. 15A through 15K show additional embodiments of a marker device. In FIGS. 15A and 15B (where internal features of the device of 15A are illustrated as ghosted), a marker device 210 consists of 6 orthogonal tapered arms 212 emanating from the center 214 of the device whereby each arm depicts a direction along the x-y-z axes. The arms 212 may be asymmetrically shaped or have features that render them asymmetric for use in marking position and/or orientation. For example, device 210 can include spherical ends 216 on certain of the arms that can be used to position the device in a known orientation relative to the patient. For example, the larger spherical end 218 may be used to identify the superior position and the smaller spherical end 220 may be used to identify the anterior position of the device. It may be desirable for individual arms/articulations to be of equal or unequal length so as to more closely fit into regular (e.g., roughly spherical) cavities or more irregular (e.g., major and minor axes of differing lengths) cavities. Other embodiments may have arms or articulations that can be adjusted in length or surface area (of the outer end) using tools or manual manipulations.

At the periphery of at least some arms, and each arm as illustrated, is a radiopaque marker such as a titanium surgical clip (locations for attaching the clips are illustrated as element 222). The clips may be in the open configuration and the closed configuration to differentiate one peripheral region from another. The specific orientation of the clip, the size of the clip, or the number of clips provided on a particular arm, can also be used to differentiate the clips, and thus the arms from one another—thereby providing another type of asymmetry that can be used to determine orientation during imaging. In use, the device may be placed in the lumpectomy cavity at the time of lumpectomy.

Figure 15C:
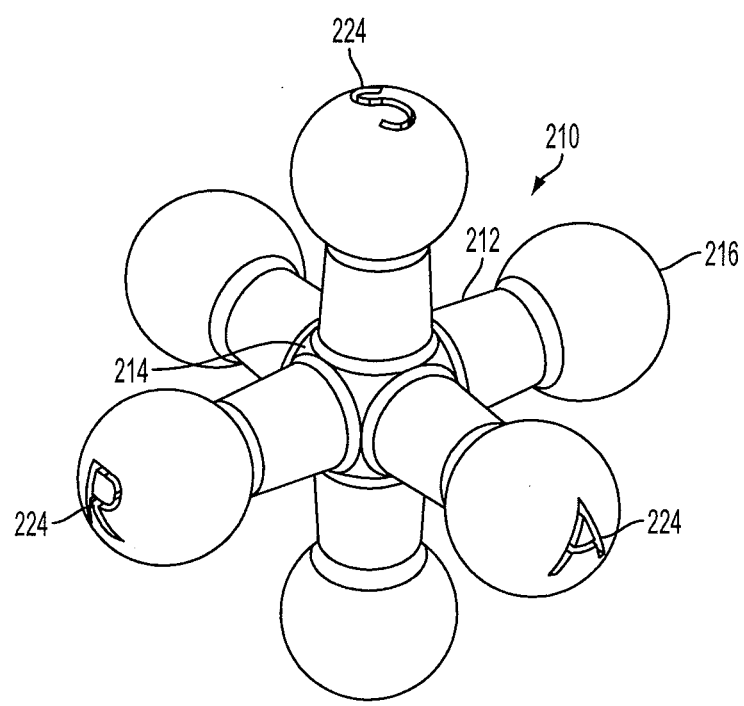
Figure 15D:
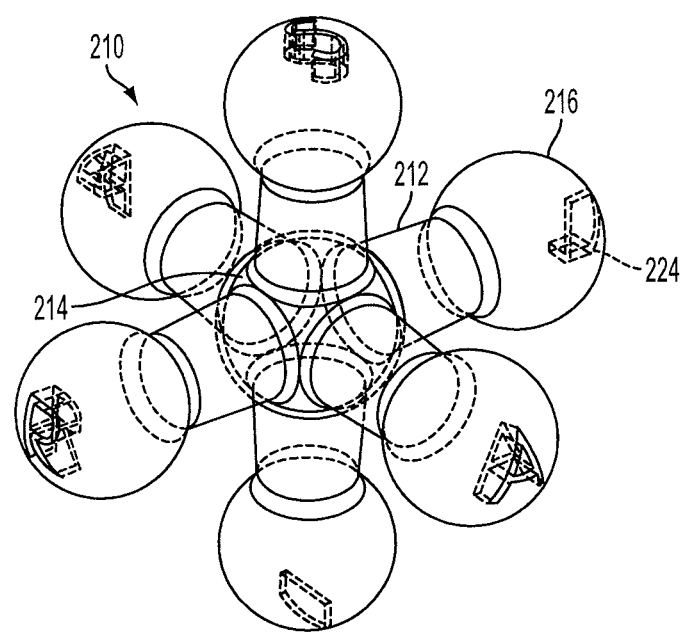
Figure 15E:
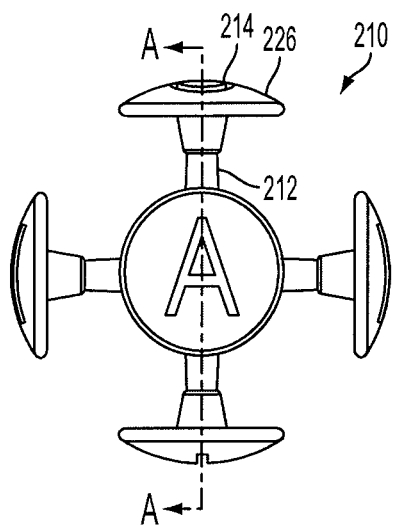
Figure 15F:
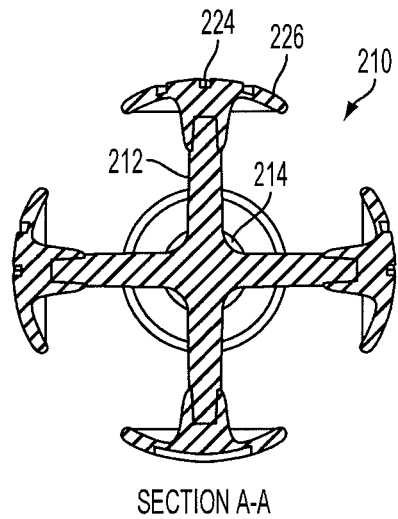
Figure 15G:
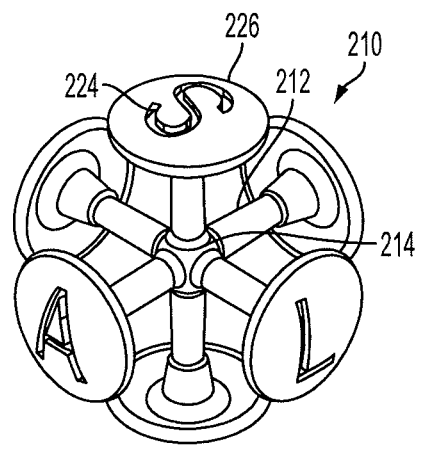
Figure 15H:
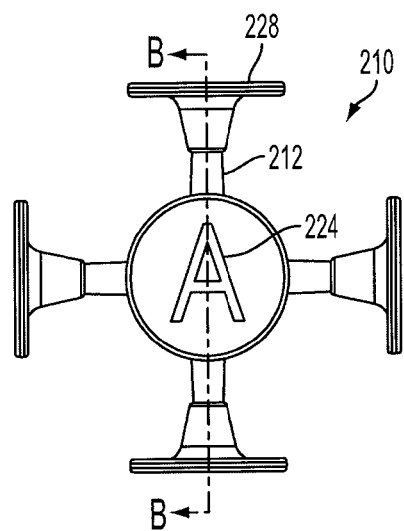
Figure 15I:
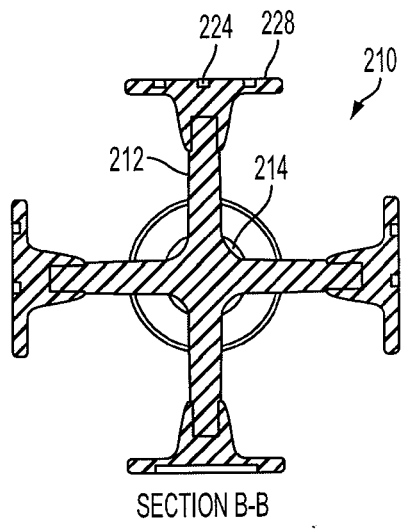
Figure 15J:
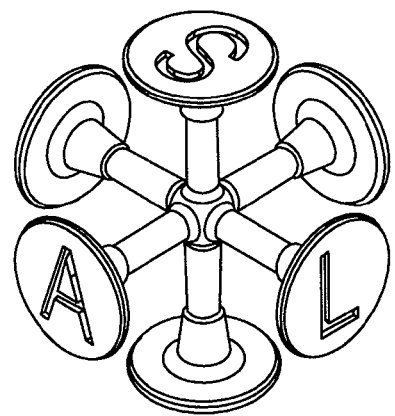

In FIGS. 15C-K the marker device can include radiopaque wire (e.g., titanium, stainless) formed into the shape of letters 224 such as A (anterior) P (posterior), S (superior), I (inferior), M (medial), L (lateral or left), and R (right). In FIGS. 15C and D, each arm 212 is provided with a sphere 216, with each of the spheres including an imageable letter indicating a direction or orientation. It should be recognized that fewer than all of the arms could have spheres and/or letters, and that other types of asymmetries, including those described above, can be combined with the illustrated use of letters. By placing the device at the time of surgery (at the time of tumor removal), the surgeon is able to visually confirm placement in the appropriate orientation because the various elements are labeled with markers relating to anatomic orientation. Thus, the portion of the device labeled "superior" will be placed in a manner that signifies the cephalad-most portion of the lumpectomy cavity. In each of its various forms, the device has elements that limit the ability to move and/or rotate, so as to maintain its position. These elements may take the form of radially protruding arms or other forms that prevent rotation by allowing the lumpectomy cavity to envelope the protrusions after placement. Suture attachment points may also be included in the arms/articulations to provide an easy means of securing the implant in the cavity.

As can be seen in FIG. 15E through K, the peripheral elements (in this case, containing the marker letters 224) of the marker device 210 comprise flat 228 (FIGS. 15H-K) or curved 226 (FIGS. 15E-G) circular caps that provide radial support against the cavity walls yet also permit partial encapsulation of the cavity wall around the element to resist rotation. This encapsulation of the element begins as the device is initially placed in the lumpectomy cavity. Fluid communication between the wall of the cavity and the cavity's interior is also permitted with these multi-arm configurations. The encapsulation continues over time as the cavity shrinks over the ensuing postoperative weeks and months. The flat or curved caps prevent rotation yet provide secure positioning of the markers at the margins of the lumpectomy cavity. In addition, the open architecture of the multi-arm embodiments allows for the free formation and resorption of seroma. As noted in the Background above, one issue facing the use of balloons and radiation is the development of persistent seroma. The embodiments of FIG. 15 can mitigate those issues.

Figure 15K:
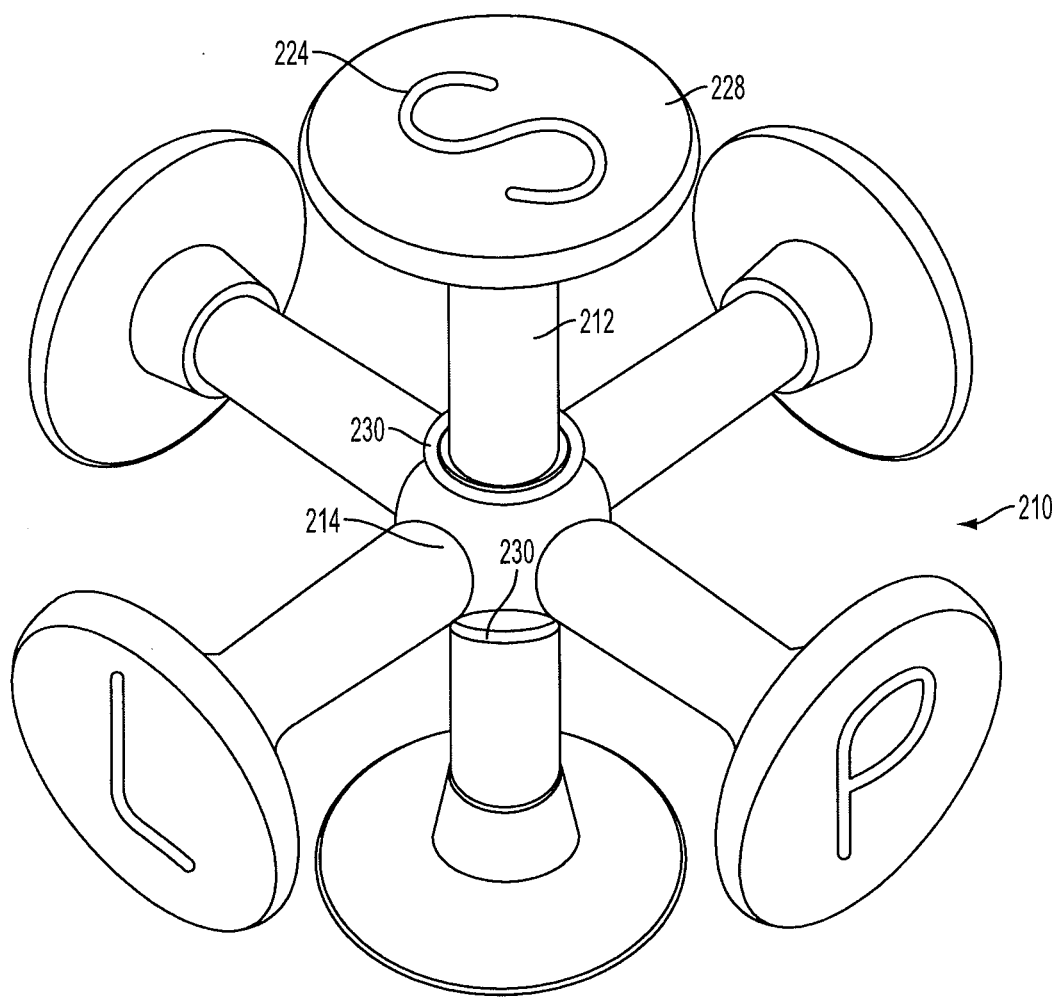

FIG. 15K illustrates a further embodiment of the marker device 210 in which two imageable rings 230 are placed at predetermined positions along one or more of the arms 212. As illustrated, the rings 230 are placed on opposed arms at positions that are equidistant from the center of the device 210. This configuration allows for a ready determining of the overall position of the device. Any number of rings could be used as desired to mark either the position or orientation of the device 210. As illustrated, the rings comprise titanium, however, other materials that are sufficiently imageable may be used and the rings may or may not be integrated into the material of the arms 212 themselves.

Figure 15L:
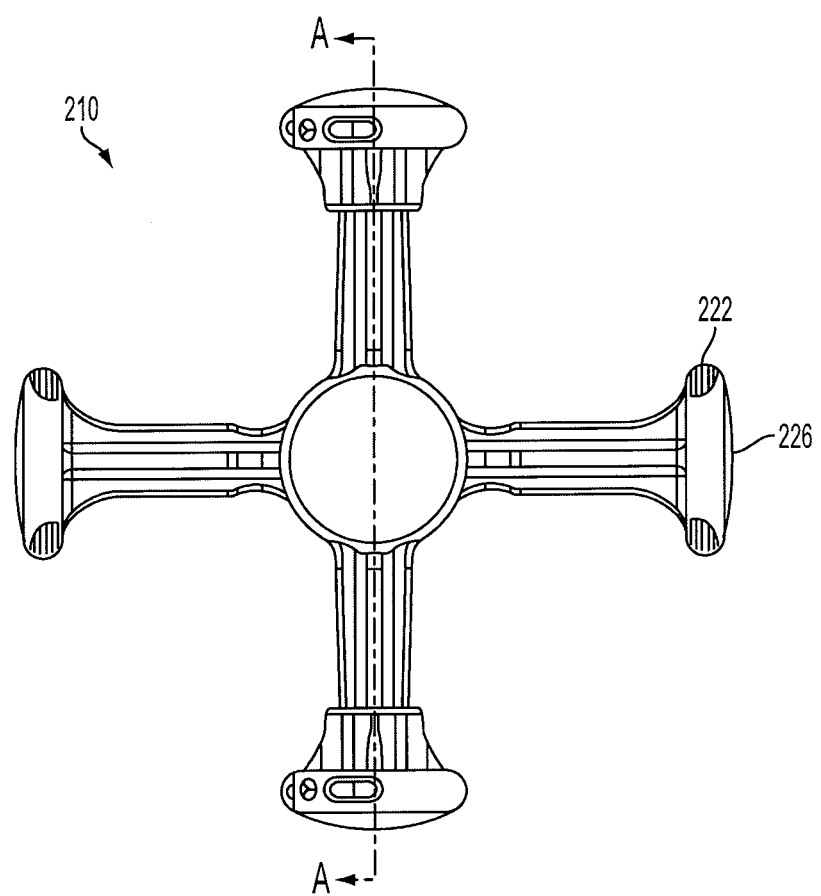
Figure 15M:
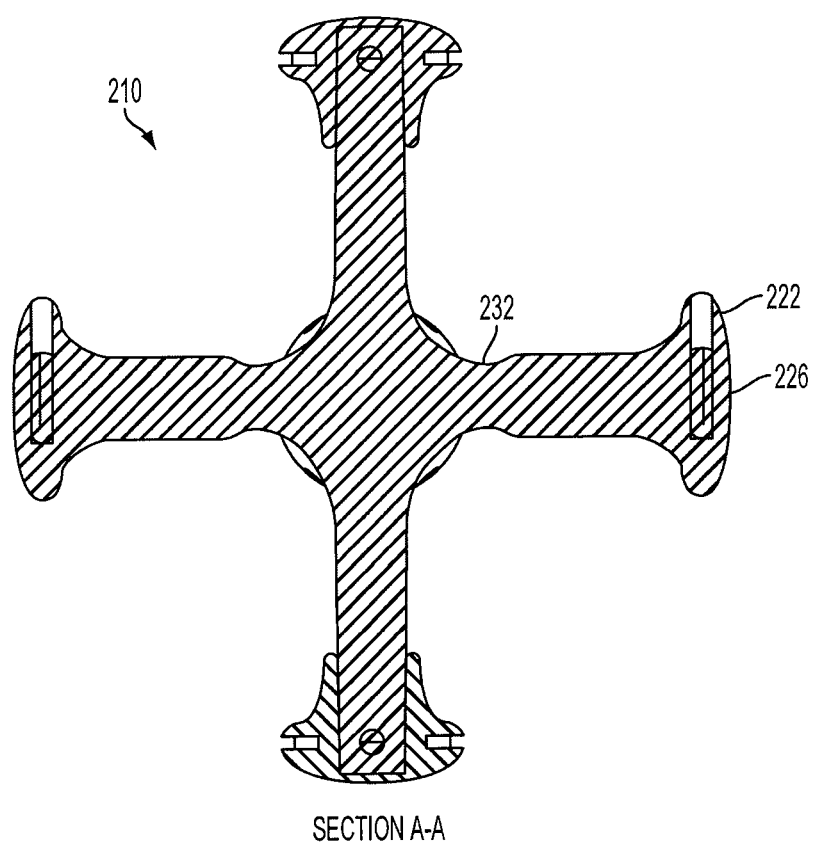
Figure 15N:
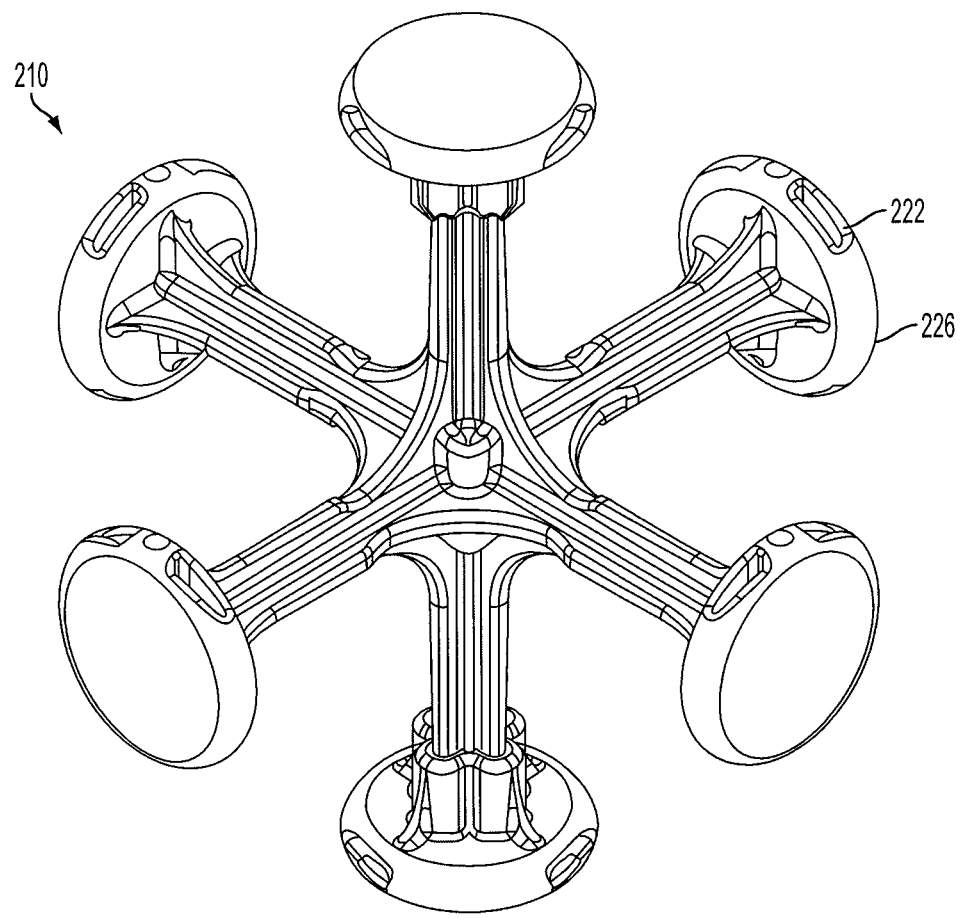

FIGS. 15L-N illustrate yet another embodiment of the marker device 210 in which the clip attachment locations 222 have been integrated into the curved circular caps 226. One of skill in the art will appreciate that any combination of the clip retention mechanisms, imageable letters, and curved or flat caps is possible. In addition, the device of FIGS. 15L-N is manufactured with four integrated end caps and only two modular end caps. This design reduces manufacturing complexity and could be applied to the other embodiments disclosed herein. This embodiment also contains indentations 232 along the arms 212 to provide a preferred zone of fracture during the in situ degradation process, to optimize comfort and safety as the embodiment is resorbed.

Figure 16:
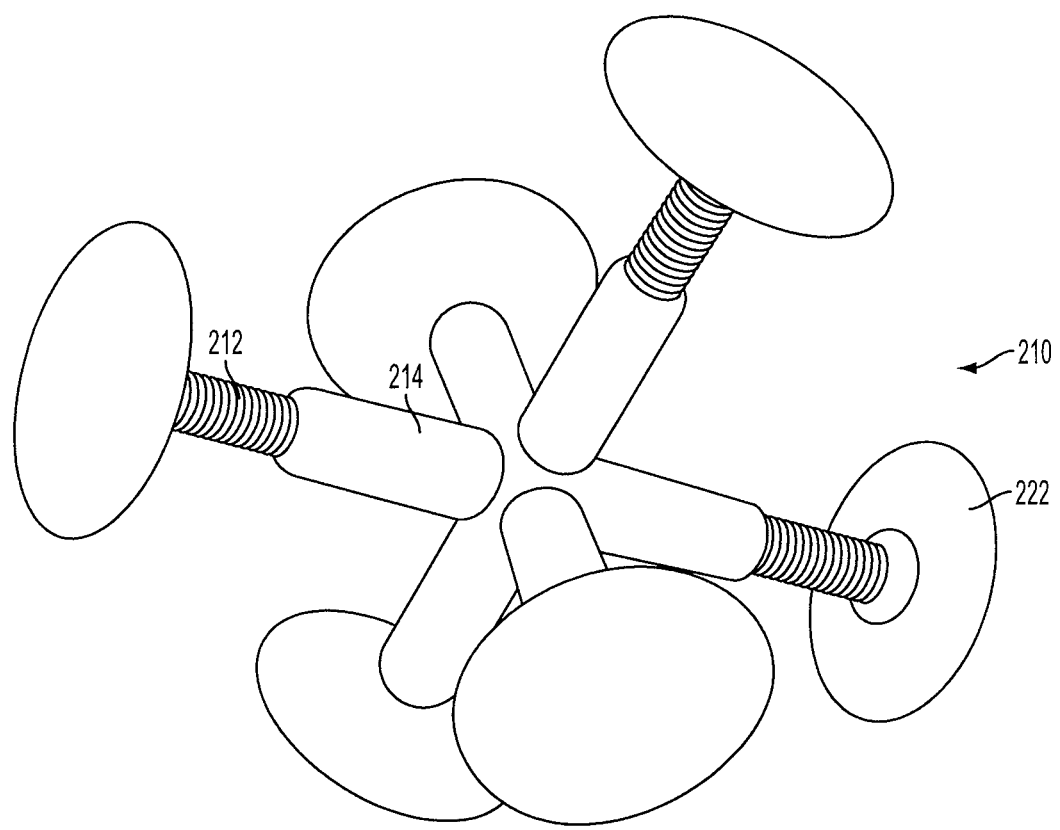
FIG. 16 shows an additional embodiment of a marker device with orthogonal radial arms extending from the center of the implant where the length of each arm can be adjusted for asymmetrical cavities.

FIG. 16 depicts an embodiment of the multi-arm marker device 210 in which each of the arms 212 can be adjusted in length to allow the device to support irregularly shaped cavities. In the embodiment shown, adjustable length is accomplished by a threaded mating between each arm 212 and the center 214. Each arm can be adjusted in length by about 1 cm in the device shown, though different ranges can be achieved depending on the overall size of the device. One of skill in the art will appreciate that adjustable length arms can be accomplished in a variety of ways besides threaded mating, for example by a sliding interface with cotter pin attachments, etc.

Adjustment of the device to fit an irregular surgical cavity can occur outside the surgical site or in situ. Surgeons can approximately adjust the device before insertion and finely adjust the device once it is in situ, or they can insert the device when it is fully collapsed to its smallest state and expand it to fill the cavity after insertion.

FIG. 16 also illustrates a feature that simplifies manufacturing of the marker device 210. In the device of FIG. 16, each end cap contains a clip attachment location 222 in the form of a through-hole. Each arm 212 similarly contains a through-hole at its distal end. Radiopaque markers (e.g., titanium, gold) in the form of rods are inserted through the holes and act as cotter pins to secure the arms and end caps together. This design can be combined with any of the methods described herein for differentiating between different radiopaque markers such as using markers of different lengths, widths, or densities in each arm.

Marker device 210 can be formed of the same materials as described above for other embodiments of marker devices, and the materials used may provide desired imaging qualities as also described above. Similarly, marker device 210 can have major dimensions (i.e., dimensions across its peripheral portions) that are the same as or similar to those described for other marker devices above.

Additionally, while not shown above, each of the marker devices described can include a feature for anchoring sutures in the event that it is desirable to do so. Such a feature could be provided by placing a through hole in a portion of the device for threading a suture (and a number of the clip retaining features described above could be used for this purpose), forming one or more loops on the device specifically for the purpose of attaching a suture, or placing a suture retaining feature on any of the clips that may be added to the outside of the devices illustrated above.

Similarly to what is stated above, the other anatomic markings follow suit once the surgeon places the device such that the superior, anterior and medial and/or lateral aspects are appropriately aligned within the lumpectomy cavity.

Following the surgical procedure, the pathologist will analyze the tumor specimen and determine if the margins (edge) of the tissue are free of tumor. If, however, the margin is positive (which can occur up to 30-40% of the time) the device will help the surgeon locate the appropriate margin for re-excision. Presently, there is no accurate method or device that allows for targeting of the re-excision margin.

This targeting can be done with radiographic guidance (mammography, ultrasound and/or MRI). The surgical site is imaged, and the visible anatomic markers will be visible and can be targeted using standard wire localization techniques, so that the surgeon has a way of locating the margin that requires re-excision. The current method of re-excision is often virtually random, as it is very difficult to identify a visible correlation of the margin that requires re-excision. Even after resorption of the device, the anatomic indicators will remain as permanent markers so that the area can be closely monitored for tumor recurrence (80% of tumors recur in the same location as the primary tumor). The above-mentioned uses are in addition to the device being used for more accurate targeting of post-operative radiation therapy.

It should be noted that during the degradation process, the circular caps may separate from the arms of the device. However, since the clips may still be contained within the caps, the clips are less likely to migrate from the lumpectomy cavity than if they were simply bare clips. In this manner, the clips are still likely to remain at the site of the lumpectomy cavity and can provide utility for helping target the external radiation beam.

In addition to external radiation, other treatments can supplement the method of the present invention. Other treatments can include supplying treatment material to the tissue surrounding the resection cavity, e.g., a chemotherapy drug, or a radiation enhancing material. Alternatively, the treatment material may be incorporated into the surface of the implant device such that after implantation the surface elutes the treatment material to surrounding tissue. In yet a further embodiment, the treatment material may be positioned on only part of the implant surface. In further embodiments, where the implant device is a bioabsorbable matrix or sponge, the treatment material may be loaded within the matrix and released as the device is absorbed. Regardless of the method of delivery, the treatment materials may include, by way of non-limiting example, a chemotherapy agent, an anti-neoplastic agent, an anti-angiogenesis agent, an immunomodulator, a hormonal agent, an immunotherapeutic agent, an antibiotic, a radiosensitizing agent, and combinations thereof.

Additional imaging techniques for localizing the implant can include EPIDs (electronic portal imaging devices), linac-mounted x-ray/fluoroscopic imaging systems, kilovoltage (KV) and megavoltage (MV) computed tomography (CT), and KV/MV cone beam CT or other non-radiographic localization systems (by way of further example, surgical navigation systems such as those marketed by BrainLab AG, or tracking systems such as those marketed by Calypso Medical Technology). Targeting of breast lesions by Cyberknife® (Accuray Incorporated) is also contemplated with the embodiments herein described.

In addition, further therapeutic energy sources (not just ionizing radiation) may be used for treatment:
  Targeting for treatment with x-rays (MV, KV) and high energy electrons (energy>1 MeV)
  HIFU,
  lithotripsy,
  external microwaves directed electromagnetic waves other than ionizing radiation While the specific examples provided relate to treatment of cancer in the breast, the devices and procedures described herein may be used for other anatomic sites, where cosmesis may or may not be necessary.

A person of ordinary skill in the art will appreciate further features and advantages of the invention based on the above-described embodiments. Accordingly, the invention is not to be limited by what has been particularly shown and described, except as indicated by the appended claims or those ultimately provided. All publications and references cited herein are expressly incorporated herein by reference in their entirety, and the invention expressly includes all combinations and sub-combinations of features included above and in the incorporated references.

The invention claimed is:

1. A device for targeting external beam radiation to a region of tissue surrounding a lumpectomy cavity comprising:
  an implant body, the implant body being formed of a bioabsorbable polymer, and comprising
    a periphery; and
    a plurality of radiopaque markers attached to the implant body about the periphery to define orthogonal x, y, and z axes of the implant body, the orthogonal x, y, and z axes having an axial length between the plurality of radiopaque markers,
    wherein the implant body includes spaced apart elements that define an open architecture that permits partial encapsulation of the cavity wall around the elements upon initial placement of the implant body within the cavity while the radiopaque markers remain in position for targeting the region of tissue surrounding the lumpectomy cavity,
    and wherein the x, y, and z axes comprise a range of axial lengths so that the implant body can be sized to fit an irregular surgical cavity.

2. The device of claim 1, wherein the radiopaque markers comprise metallic clips.

3. The device of claim 1, wherein the bioabsorbable polymer has an absorption time of at least 2 weeks.

4. The device of claim 3, wherein the bioabsorbable polymer has an absorption time of at least 6 months.

5. The device of claim 1, wherein the bioabsorbable polymer is thermoplastic.

6. The device of claim 1, further comprising one or more protrusions for bluntly penetrating into surrounding tissue.

7. The device of claim 1, wherein the radiopaque markers allow visualization by radiography.

8. The device of claim 7, wherein the radiography includes mega-voltage x-rays.

9. The device of claim 7, wherein the radiography includes kilo-voltage x-rays.

10. The device of claim 7, wherein the radiography includes fluoroscopy.

11. A device for targeting external beam radiation to regions of target tissue surrounding a tumor resection cavity comprising:
  an implant body, the implant body having an open architecture and being formed of a bioabsorbable material, and comprising a periphery; and
  a plurality of radiopaque markers attached to the implant body about the periphery to define orthogonal x, y, and z axes of the implant body, the orthogonal x, y, and z axes having an axial length between the plurality of radiopaque markers,
    wherein the open architecture implant body supports a wall of the cavity yet also permits partial encapsulation of the cavity wall around the body upon initial placement of the body within the cavity, and
  wherein the x, y, and z axes comprise a range of axial lengths so that the implant body can be sized to fit an irregular surgical cavity.

12. The device of claim 11, wherein the radiopaque markers comprise surgical clips.

13. The device of claim 11, wherein the bioabsorbable material is a thermoplastic polymer.

14. The device of claim 11, further comprising one or more protrusions for bluntly penetrating into surrounding tissue.

15. The device of claim 11, wherein the bioabsorbable material has an absorption time of at least 2 weeks.

16. The device of claim 15, wherein the bioabsorbable material has an absorption time of at least 6 months.

* * * * *